(12) United States Patent
Knapp

(10) Patent No.: US 7,803,975 B2
(45) Date of Patent: Sep. 28, 2010

(54) PROCESS FOR SEPARATING A FLUOROOLEFIN FROM HF BY LIQUID-LIQUID EXTRACTION

(75) Inventor: Jeffrey P. Knapp, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/827,209

(22) Filed: Jul. 11, 2007

(65) Prior Publication Data

US 2008/0011678 A1   Jan. 17, 2008

Related U.S. Application Data

(60) Provisional application No. 60/830,938, filed on Jul. 13, 2006.

(51) Int. Cl.
C07C 17/38 (2006.01)
C07C 21/18 (2006.01)

(52) U.S. Cl. .................... 570/177; 570/136

(58) Field of Classification Search ............ None
See application file for complete search history.

(56) References Cited

U.S. PATENT DOCUMENTS

| | | | |
|---|---|---|---|
| 5,560,899 A | 10/1996 | Solinas et al. | |
| 5,744,662 A | 4/1998 | Moallemi | |
| 5,874,658 A | 2/1999 | Belter | |
| 5,895,639 A | 4/1999 | Swain et al. | |
| 6,031,141 A | 2/2000 | Mallikarjuna | |
| 6,066,768 A | 5/2000 | Nappa et al. | |
| 6,156,944 A | 12/2000 | Pham et al. | |
| 6,294,055 B2 | 9/2001 | Herkelmann et al. | |
| 6,407,297 B1 | 6/2002 | Ewing | |
| 2001/0004961 A1* | 6/2001 | Herkelmann et al. | ......... 203/43 |
| 2004/0236160 A1 | 11/2004 | Tung et al. | |
| 2007/0100175 A1 | 5/2007 | Miller et al. | |

FOREIGN PATENT DOCUMENTS

JP        0921109        6/1999

* cited by examiner

*Primary Examiner*—Karl J Puttlitz

(57) ABSTRACT

Disclosed is a process for separating fluoroolefin from a composition comprising HF and fluoroolefin, said process comprising extracting said composition with an extractant. Also disclosed is a composition comprising HF, at least one fluoroolefin, and at least one extractant.

17 Claims, 2 Drawing Sheets

PROCESS FOR SEPARATING A FLUOROOLEFIN FROM HF BY LIQUID-LIQUID EXTRACTION

CROSS REFERENCE(S) TO RELATED APPLICATION(S)

This application claims the priority benefit of U.S. Provisional Application No. 60/830,938, filed Jul. 13, 2006.

BACKGROUND OF THE INVENTION

1. Field of the Disclosure

This disclosure relates in general to a process for the separation of hydrogen fluoride from fluoroolefins by extraction. In particular, the process for separation of hydrogen fluoride from fluoroolefins comprises liquid-liquid extraction 2. Description of the Related Art The chemical manufacture of fluoroolefins often produces mixtures of the desired fluoroolefins and hydrogen fluoride (HF). The separation of fluoroolefins from these mixtures is not always easily accomplished because many fluoroolefins form an azeotrope with HF. Existing methods of distillation and decantation are very often ineffective for the separation of these compounds. Aqueous scrubbing may be effective, but requires the use of large amounts of scrubbing solutions and produces excessive waste and a wet product that must then be dried.

WO 98/00379 discloses the use of sulfuric acid as extractant to separate HF from a fluorocarbon (e.g. HFC-245fa or HFC-356mcfq) by preferentially extracting the HF into the sulfuric acid phase. WO 98/00380 discloses a similar extraction process utilizing water to preferentially extract the HF. US 2001/0004961 A1 discloses the use of hydrocarbon and halocarbon solvents to remove HF from mixtures with hydrofluoroalkanes of formula $C_aH_{(2a+2)-b}F_b$, wherein a=3 to 6 and b=1 to 2a+1, by liquid-liquid extraction.

Some fluoroolefins have been found to form azeotropes with hydrogen fluoride, complicating their separation. Aqueous and caustic scrubbing can be effective, but the valuable HF is converted to a waste and additional equipment is needed to dry the wet fluoroolefin produced. Therefore, there is a need for new methods of separating fluoroolefins from HF.

SUMMARY OF THE INVENTION

The present disclosure relates to a process for separating a fluoroolefin from a composition comprising HF and fluoroolefin, said process comprising extracting said composition with an extractant.

The present disclosure further relates to a composition comprising HF, at least one fluoroolefin, and at least one extractant.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
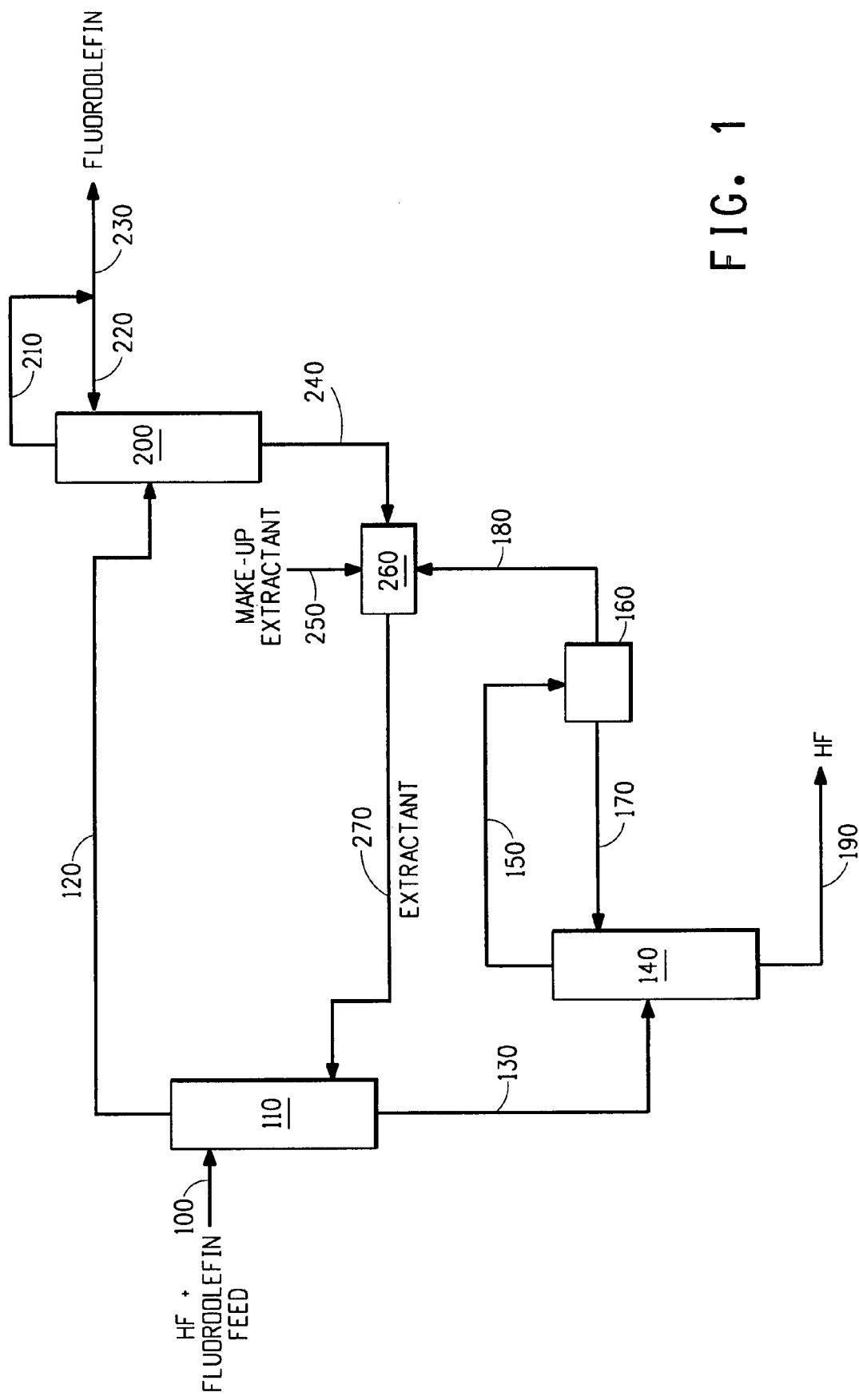
FIG. 1 includes an illustration of a process to separate fluoroolefin from a composition comprising HF and fluoroolefin by liquid-liquid extraction wherein the extractant has a lower density than the composition comprising HF and fluoroolefin.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION OF THE INVENTION

The present disclosure relates to a process for separating a fluoroolefin from a composition comprising HF and fluoroolefin, said process comprising extracting said composition with an extractant.

In one embodiment, the process for separating a fluoroolefin from a composition comprising HF and fluoroolefin by extracting said composition with an extractant, wherein said extracting comprises a liquid-liquid extraction.

In one embodiment, the process for separating fluoroolefin from a composition comprising HF and fluoroolefin by extracting said composition with an extractant, may use extractants selected from the group consisting of hydrocarbons, chlorocarbons, chlorofluorocarbons, hydrochlorofluorocarbons, hydrofluorocarbons, perfluorocarbons, and perfluorinated ethers.

In one embodiment the process for separating fluoroolefin from a composition comprising HF and fluoroolefin, comprises:
  a. feeding a composition comprising HF and fluoroolefin and a composition comprising extractant to an extractor; and
  b. removing from said extractor an extractant-rich phase comprising extractant and fluoroolefin.

Optionally, in another embodiment the process for separating fluoroolefin from a composition comprising HF and fluoroolefin further comprises:
  a. feeding the extractant-rich phase comprising extractant and fluoroolefin to an extractant recovery column; and
  b. recovering fluoroolefin product essentially free of extractant from the extractant recovery column.

In another embodiment the process separating fluoroolefin from a composition comprising HF and fluoroolefin comprises:
  a. feeding a composition comprising HF and fluoroolefin and a composition comprising extractant to an extractor; and
  b. removing from said extractor an HF-rich phase.

Optionally, in another embodiment the process for separating fluoroolefin from a composition comprising HF and fluoroolefin further comprises:
  a. feeding said HF-rich phase to a raffinate stripping column; and
  b. recovering from said raffinate stripping column an HF product essentially free of fluoroolefin and extractant.

In yet another embodiment the process for separating fluoroolefin from a composition comprising HF and fluoroolefin comprises:
  a. feeding a composition comprising HF and fluoroolefin and a composition comprising extractant to an extractor;
  b. removing from said extractor an extractant-rich phase comprising extractant and fluoroolefin;
  c. removing from said extractor an HF-rich phase;
  d. feeding said extractant-rich phase comprising extractant and fluoroolefin to an extractant recovery column;

e. recovering fluoroolefin product essentially free of extractant from the extractant recovery column;
f. feeding said HF-rich phase to a raffinate stripping column
g. recovering from said raffinate stripping column HF product essentially free of fluoroolefin and extractant.

In one embodiment, said extractor operates at a pressure of from about 14.7 psia to about 300 psia and a temperature from about −50° C. to about 150° C.

In one embodiment, said extractant recovery column operates at a pressure of about 14.7 psia to about 300 psia and a top temperature of about −50° C. to about 100° C. and a bottom temperature of about 50° C. to about 250° C.

In one embodiment, said raffinate stripping column operates at a pressure of about 14.7 psia to about 100 psia and a top temperature of about −50° C. to about 90° C. and a bottom temperature from about 20° C. to about 150° C.

The present disclosure further provides a composition comprising:
a. HF,
b. at least one fluoroolefin, and
c. at least one extractant.

In one embodiment, the extractant may be at/least one compound selected from the group consisting of hydrocarbons, chlorocarbons, chlorofluorocarbons, hydrochlorofluorocarbons, hydrofluorocarbons, perfluorocarbons, and perfluorinated ethers.

In some embodiments, said fluoroolefin is selected from the group consisting of:
(i) fluoroolefins of the formula E- or Z—$R^1$CH=CH$R^2$, wherein $R^1$ and $R^2$ are, independently, $C_1$ to $C_6$ perfluoroalkyl groups;
(ii) cyclic fluoroolefins of the formula cyclo-[CX=CY(CZW)$_n$—], wherein X, Y, Z, and W, independently, are H or F, and n is an integer from 2 to 5; and
(iii) fluoroolefins selected from the group consisting of: tetrafluoroethylene ($CF_2$=$CF_2$); hexafluoropropene ($CF_3CF$=$CF_2$); 1,2,3,3,3-pentafluoro-1-propene (CHF=$CFCF_3$), 1,1,3,3,3-pentafluoro-1-propene ($CF_2$=$CHCF_3$), 1,1,2,3,3-pentafluoro-1-propene ($CF_2$=$CFCHF_2$), 1,2,3,3-tetrafluoro-1-propene (CHF=$CFCHF_2$), 2,3,3,3-tetrafluoro-1-propene ($CH_2$=$CFCF_3$), 1,3,3,3-tetrafluoro-1-propeneCHF=$CHCF_3$), 1,1,2,3-tetrafluoro-1-propene ($CF_2$=$CFCH_2F$), 1,1,3,3-tetrafluoro-1-propene ($CF_2$=$CHCHF_2$), 1,2,3,3-tetrafluoro-1-propene (CHF=$CFCHF_2$), 3,3,3-trifluoro-1-propene ($CH_2$=$CHCF_3$), 2,3,3-trifluoro-1-propene ($CHF_2CF$=$CH_2$); 1,1,2-trifluoro-1-propene ($CH_3CF$=$CF_2$); 1,2,3-trifluoro-1-propene ($CH_2FCF$=$CF_2$); 1,1,3-trifluoro-1-propene ($CH_2FCH$=$CF_2$); 1,3,3-trifluoro-1-propene ($CHF_2CH$=CHF); 1,1,1,2,3,4,4,4-octafluoro-2-butene ($CF_3CF$=$CFCF_3$); 1,1,2,3,3,4,4,4-octafluoro-1-butene ($CF_3CF_2CF$=$CF_2$); 1,1,1,2,4,4,4-heptafluoro-2-butene ($CF_3CF$=$CHCF_3$); 1,2,3,3,4,4,4-heptafluoro-1-butene (CHF=$CFCF_2CF_3$); 1,1,2,3,4,4-heptafluoro-2-butene ($CHF_2CF$=$CFCF_3$); 1,3,3,3-tetrafluoro-2-(trifluoromethyl)-1-propene (($CF_3$)$_2$C=CHF); 1,1,3,3,4,4-heptafluoro-1-butene ($CF_2$=$CHCF_2CF_3$); 1,1,2,3,4,4,4-heptafluoro-1-butene ($CF_2$=$CFCHFCF_3$); 1,1,2,3,3,4,4-heptafluoro-1-butene ($CF_2$=$CFCF_2CHF_2$); 2,3,3,4,4,4-hexafluoro-1-butene ($CF_3CF_2CF$=$CH_2$); 1,3,3,4,4,4-hexafluoro-1-butene (CHF=$CHCF_2CF_3$); 1,2,3,4,4,4-hexafluoro-1-butene (CHF=$CFCHFCF_3$); 1,2,3,3,4,4-hexafluoro-1-butene (CHF=$CFCF_2CHF_2$); 1,1,2,3,4,4-hexafluoro-2-butene ($CHF_2CF$=$CFCHF_2$); 1,1,1,2,3,4-hexafluoro-2-butene ($CH_2FCF$=$CFCF_3$); 1,1,1,2,4,4-hexafluoro-2-butene ($CHF_2CH$=$CFCF_3$); 1,1,3,4,4-hexafluoro-2-butene ($CF_3CH$=$CFCHF_2$); 1,1,2,3,3,4-hexafluoro-1-butene ($CF_2$=$CFCF_2CH_2F$); 1,1,2,3,4,4-hexafluoro-1-butene ($CF_2$=$CFCHFCHF_2$); 3,3,3-trifluoro-2-(trifluoromethyl)-1-propene ($CH_2$=C($CF_3$)$_2$); 1,1,1,2,4-pentafluoro-2-butene ($CH_2FCH$=$CFCF_3$); 1,1,1,3,4-pentafluoro-2-butene ($CF_3CH$=$CFCH_2F$); 3,3,4,4,4-pentafluoro-1-butene ($CF_3CF_2CH$=$CH_2$); 1,1,1,4,4-pentafluoro-2-butene ($CHF_2CH$=$CHCF_3$); 1,1,1,2,3-pentafluoro-2-butene ($CH_3CF$=$CFCF_3$); 2,3,3,4,4-pentafluoro-1-butene ($CH_2$=$CFCF_2CHF_2$); 1,1,2,4,4-pentafluoro-2-butene ($CHF_2CF$=$CHCHF_2$); 1,1,2,3,3-pentafluoro-1-butene ($CH_3CF_2CF$=$CF_2$); 1,1,2,3,4-pentafluoro-2-butene ($CH_2FCF$=$CFCHF_2$); 1,1,3,3,3-pentafluoro-2-methyl-1-propene ($CF_2$=C($CF_3$)($CH_3$)); 2-(difluoromethyl)-3,3,3-trifluoro-1-propene ($CH_2$=C($CHF_2$)($CF_3$)); 2,3,4,4,4-pentafluoro-1-butene (CHF=$CFCHFCF_3$); 1,2,4,4,4-pentafluoro-1-butene (CHF=$CFCH_2CF_3$); 1,3,4,4,4-pentafluoro-1-butene (CHF=$CHCHFCF_3$); 1,3,3,4,4-pentafluoro-1-butene (CHF=$CHCF_2CHF_2$); 1,2,3,4,4-pentafluoro-1-butene (CHF=$CFCHFCHF_2$); 3,3,4,4-tetrafluoro-1-butene ($CH_2$=$CHCF_2CHF_2$); 1,1-difluoro-2-(difluoromethyl)-1-propene ($CF_2$=C($CHF_2$)($CH_3$)); 1,3,3,3-tetrafluoro-2-methyl-1-propene (CHF=C($CF_3$)($CH_3$)); 3,3-difluoro-2-(difluoromethyl)-1-propene ($CH_2$=C($CHF_2$)$_2$); 1,1,1,2-tetrafluoro-2-butene ($CF_3CF$=$CHCH_3$); 1,1,1,3-tetrafluoro-2-butene ($CH_3CF$=$CHCF_3$); 1,1,1,2,3,4,4,5,5,5-decafluoro-2-pentene ($CF_3CF$=$CFCF_2CF_3$); 1,1,2,3,3,4,4,5,5,5-decafluoro-1-pentene ($CF_2$=$CFCF_2CF_2CF_3$); 1,1,1,4,4,4-hexafluoro-2-(trifluoromethyl)-2-butene (($CF_3$)$_2$C=$CHCF_3$); 1,1,1,2,4,4,5,5,5-nonafluoro-2-pentene ($CF_3CF$=$CHCF_2CF_3$); 1,1,1,3,4,4,5,5,5-nonafluoro-2-pentene ($CF_3CH$=$CFCF_2CF_3$); 1,2,3,3,4,4,5,5,5-nonafluoro-1-pentene (CHF=$CFCF_2CF_2CF_3$); 1,1,3,3,4,4,5,5,5-nonafluoro-1-pentene ($CF_2$=$CHCF_2CF_2CF_3$); 1,1,2,3,3,4,4,5,5-nonafluoro-1-pentene ($CF_2$=$CFCF_2CF_2CHF_2$); 1,1,2,3,4,4,5,5,5-nonafluoro-2-pentene ($CHF_2CF$=$CFCF_2CF_3$); 1,1,1,2,3,4,4,5,5-nonafluoro-2-pentene ($CF_3CF$=$CFCF_2CHF_2$); 1,1,1,2,3,4,5,5,5-nonafluoro-2-pentene ($CF_3CF$=$CFCHFCF_3$); 1,2,3,3,4,4-hexafluoro-3-(trifluoromethyl)-1-butene (CHF=$CFCF(CF_3)_2$); 1,1,2,4,4,4-hexafluoro-3-(trifluoromethyl)-1-butene ($CF_2$=$CFCH(CF_3)_2$); 1,1,1,4,4,4-hexafluoro-2-(trifluoromethyl)-2-butene ($CF_3CH$=C($CF_3$)$_2$); 1,1,3,4,4,4-hexafluoro-3-(trifluoromethyl)-1-butene ($CF_2$=$CHCF(CF_3)_2$); 2,3,3,4,4,5,5,5-octafluoro-1-pentene ($CH_2$=$CFCF_2CF_2CF_3$); 1,2,3,3,4,4,5,5-octafluoro-1-pentene (CHF=$CFCF_2CF_2CHF_2$); 3,3,4,4-pentafluoro-2-(trifluoromethyl)-1-butene ($CH_2$=C($CF_3$)$CF_2CF_3$); 1,1,4,4,4-pentafluoro-3-(trifluoromethyl)-1-butene ($CF_2$=$CHCH(CF_3)_2$); 1,3,4,4,4-pentafluoro-3-(trifluoromethyl)-1-butene (CHF=$CHCF(CF_3)_2$); 1,1,4,4,4-pentafluoro-2-(trifluoromethyl)-1-butene ($CF_2$=C($CF_3$)$CH_2CF_3$); 3,4,4,4-tetrafluoro-3-(trifluoromethyl)-1-butene (($CF_3$)$_2$CFCH=$CH_2$); 3,3,4,4,5,5,5-heptafluoro-1-pentene ($CF_3CF_2CF_2CH$=$CH_2$); 2,3,3,4,4,5,5-heptafluoro-1-pentene ($CH_2$=$CFCF_2CF_2CHF_2$); 1,1,3,3,5,5,5-heptafluoro-1-butene ($CF_2$=$CHCF_2CH_2CF_3$); 1,1,1,2,4,4,4-heptafluoro-3-methyl-2-butene ($CF_3CF$=C($CF_3$)($CH_3$)); 2,4,4,4-tetrafluoro-3-(trifluoromethyl)-1-butene ($CH_2$=$CFCH(CF_3)_2$); 1,4,4,4-tetrafluoro-3-(trifluoromethyl)-1-butene (CHF=$CHCH(CF_3)_2$); 1,1,1,4-tetrafluoro-2-(trifluoromethyl)-2-butene ($CH_2FCH$=C($CF_3$)$_2$); 1,1,1,3-tetrafluoro-2-(trifluoromethyl)-2-butene ($CH_3CF$=C($CF_3$)$_2$); 1,1,1-trifluoro-2-(trifluoromethyl)-2-butene ((CF$_3$)$_2$C=CHCH$_3$); 3,4,4,5,5,5-hexafluoro-2-pentene (CF$_3$CF$_2$CF=CHCH$_3$); 1,1,1,4,4,4-hexafluoro-2-methyl-2-butene (CF$_3$C(CH$_3$)=CHCF$_3$); 3,3,4,5,5,5-hexafluoro-1-pentene (CH$_2$=CHCF$_2$CHFCF$_3$); 4,4,4-trifluoro-2-(trifluoromethyl)-1-butene (CH$_2$=C(CF$_3$)CH$_2$CF$_3$); 1,1,2,3,3,4,4,5,5,6,6,6-dodecafluoro-1-hexene (CF$_3$(CF$_2$)$_3$CF=CF$_2$); 1,1,1,2,2,3,4,5,5,6,6,6-dodecafluoro-3-hexene (CF$_3$CF$_2$CF=CFCF$_2$CF$_3$); 1,1,1,4,4,4-hexafluoro-2,3-bis(trifluoromethyl)-2-butene ((CF$_3$)$_2$C=C(CF$_3$)$_2$); 1,1,1,2,3,4,5,5,5-nonafluoro-4-(trifluoromethyl)-2-pentene ((CF$_3$)$_2$CFCF=CFCF$_3$); 1,1,1,4,4,5,5,5-octafluoro-2-(trifluoromethyl)-2-pentene ((CF$_3$)$_2$C=CHC$_2$F$_5$); 1,1,1,3,4,5,5,5-octafluoro-4-(trifluoromethyl)-2-pentene ((CF$_3$)$_2$CFCF=CHCF$_3$); 3,3,4,4,5,5,6,6,6-nonafluoro-1-hexene (CF$_3$CF$_2$CF$_2$CF$_2$CH=CH$_2$); 4,4,4-trifluoro-3,3-bis(trifluoromethyl)-1-butene (CH$_2$=CHC(CF$_3$)$_3$); 1,1,1,4,4,4-hexafluoro-3-methyl-2-(trifluoromethyl)-2-butene ((CF$_3$)$_2$C=C(CH$_3$)(CF$_3$)); 2,3,3,5,5,5-hexafluoro-4-(trifluoromethyl)-1-pentene (CH$_2$=CFCF$_2$CH(CF$_3$)$_2$); 1,1,1,2,4,4,5,5,5-nonafluoro-3-methyl-2-pentene (CF$_3$CF=C(CH$_3$)CF$_2$CF$_3$); 1,1,1,5,5,5-hexafluoro-4-(trifluoromethyl)-2-pentene (CF$_3$CH=CHCH(CF$_3$)$_2$); 3,4,4,5,5,6,6,6-octafluoro-2-hexene (CF$_3$CF$_2$CF$_2$CF=CHCH$_3$); 3,3,4,4,5,5,6,6-octafluoro1-hexene (CH$_2$=CHCF$_2$CF$_2$CF$_2$CHF$_2$); 1,1,1,4,4-pentafluoro-2-(trifluoromethyl)-2-pentene ((CF$_3$)$_2$C=CHCF$_2$CH$_3$); 4,4,5,5,5-pentafluoro-2-(trifluoromethyl)-1-pentene (CH$_2$=C(CF$_3$)CH$_2$C$_2$F$_5$); 3,3,4,4,5,5,5-heptafluoro-2-methyl-1-pentene (CF$_3$CF$_2$CF$_2$C(CH$_3$)=CH$_2$); 4,4,5,5,6,6,6-heptafluoro-2-hexene (CF$_3$CF$_2$CF$_2$CH=CHCH$_3$); 4,4,5,5,6,6,6-heptafluoro-1-hexene (CH$_2$=CHCH$_2$CF$_2$C$_2$F$_5$); 1,1,1,2,2,3,4-heptafluoro-3-hexene (CF$_3$CF$_2$CF=CFC$_2$H$_5$); 4,5,5,5-tetrafluoro-4-(trifluoromethyl)-1-pentene (CH$_2$=CHCH$_2$CF(CF$_3$)$_2$); 1,1,1,2,5,5,5-heptafluoro-4-methyl-2-pentene (CF$_3$CF=CHCH(CF$_3$)(CH$_3$)); 1,1,1,3-tetrafluoro-2-(trifluoromethyl)-2-pentene ((CF$_3$)$_2$C=CFC$_2$H$_5$); 1,1,1,2,3,4,4,5,5,6,6,7,7,7-tetradecafluoro-2-heptene (CF$_3$CF=CFCF$_2$CF$_2$C$_2$F$_5$); 1,1,1,2,2,3,4,5,5,6,6,7,7,7-tetradecafluoro-3-heptene (CF$_3$CF$_2$CF=CFCF$_2$C$_2$F$_5$); 1,1,1,3,4,4,5,5,6,6,7,7,7-tridecafluoro-2-heptene (CF$_3$CH=CFCF$_2$CF$_2$C$_2$F$_5$); 1,1,1,2,4,4,5,5,6,6,7,7,7-tridecafluoro-2-heptene (CF$_3$CF=CHCF$_2$CF$_2$C$_2$F$_5$); 1,1,1,2,2,4,5,5,6,6,7,7,7-tridecafluoro-3-heptene (CF$_3$CF$_2$CH=CFCF$_2$C$_2$F$_5$); and 1,1,1,2,2,3,5,5,6,6,7,7,7-tridecafluoro-3-heptene (CF$_3$CF$_2$CF=CHCF$_2$C$_2$F$_5$).

In certain embodiments, said extractant is selected from the group consisting of:

ethane, ethylene, n-propane, propylene, n-butane, isobutane, cyclobutane, 1-butene, 2-butene (cis or trans), n-pentane, isopentane (2-methylbutane), neopentane (2,2-dimethylpropane), cyclopentane, 1-pentene, 2-pentene (cis or trans), cyclopentene, n-hexane, cyclohexane, 2-methylpentane, 3-methylpentane, 1-hexene, 2-hexene (cis or trans), 3-hexene (cis or trans), neohexane (2,2-dimethylbutane), neohexene (3,3-dimethyl-1-butene), 2,2-dimethylbutane, 2,3-dimethylbutane, 2,3-dimethyl-2-butene, 2,3-dimethyl-1-butene, 3,3-dimethyl-1-butene, n-heptane, 1-heptene, 2-heptene (cis or trans), 3-heptene (cis or trans), cycloheptene, octane (all isomers), nonane (all isomers), decane (all isomers), undecane (all isomers), dodecane (all isomers), benzene, toluene, tetrachloroethylene, trichloroethylene, 1,1-dichloroethylene, 1,2-dichloroethylene, carbon tetrachloride (tetrachloromethane), chloroform (trichloromethane), methylene chloride (dichloromethane), 1,1,2,2-tetrachloroethane, 1,1,1,2-tetrachloroethane, 1,1,2-trichloroethane, 1,1,1-trichloroethane, 1,1,1,3,3,3-hexachloropropane, dichlorodifluoromethane (CFC-12), fluorotrichloromethane (CFC-11), fluoropentachloroethane (CFC-111), 1,2-difluoro-1,1,2,2-tetrachloroethane (CFC-112), 1,1-difluoro-1,2,2,2-tetrachloroethane (CFC-112a), 1,1,2-trichloro-1,2,2-trifluoroethane (CFC-113), 1,1,1-trichloro-2,2,2-trifluoroethane (CFC-113a), 1,2-dichloro-1,1,2,2-tetrafluoroethane (CFC-114), 1,1-dichloro-1,2,2,2-tetrafluoroethane (CFC-114a), and chloropentafluoroethane (CFC-115), 1,1,1,2,3-pentafluoro-2,3,3-trichloropropane (CFC-215bb), 2,2-dichloro-1,1,1,3,3,3-hexafluoropropane (CFC-216aa), 2,3-dichloro-1,1,1,2,3,3-hexafluoropropane (CFC-216ba), 2-chloro-1,1,1,2,3,3,3-heptafluoropropane (CFC-217ba), dichlorofluoromethane (HCFC-21), 1,1,2-trichloro-2,2-difluoroethane (HCFC-122), 2,2-dichloro-1,1,1-trifluoroethane (HCFC-123), 1,2-dichloro-1,1,1-trifluoroethane (HCFC-123a), 2-chloro-1,1,1,2-tetrafluoroethane (HCFC-124), 1-chloro-1,1,2,2-tetrafluoroethane (HCFC-124a), 1-chloro-1,2,2-trifluoroethane (HCFC-133), 2-chloro-1,1,1-trifluoroethane (HCFC-133a), 1,1-dichloro-2-fluoroethane (HCFC-141a), 1,1-dichloro-1-fluoroethane (HCFC-141b), 1-chloro-1,2-difluoroethane (HCFC-142a), 1-chloro-1,1-difluoroethane (HCFC-142b), 1,1,1,2,2,3,4,5,5,6,6,7,7,7-tetradecafluoroheptane (HFC-63-14mcee), 3,3,4,4,5,5,6,6-nonafluoro-1-hexene, HFC-162-13mczy, 1,2,3,3,3-pentafluoro-1-propene (HFC-1225ye), 1,1,3,3,3-pentafluoro-1-propene (HFC-1225zc), 1,3,3,3-tetrafluoro-1-propene (HFC-1234ze), 2,3,3,3-tetrafluoro-1-propene (HFC-1234yf), 3,3,3-trifluoro-1-propene (HFC-1243zf), 1,1,1,2,4,4,5,5,5-nonafluoro-2-pentene (HFC-1429myz), 1,1,1,3,4,4,5,5,5-nonafluoro-2-pentene (HFC-1429mzy), 1,1,1,4,4,4-hexafluoro-2-butene (F11E), 1,1,1,4,4,5,5,5-octafluoro-2-pentene (F12E), 1,1,1,2,2,5,5,6,6,7,7,8,8,8-tetradecafluoro-3-octene (F24E), 1,1,1,2,2,3,3,6,6,7,7,8,8,8-tetradecafluoro-4-octene (F33E), fluorobenzene, octafluoropropane (PFC-218), octafluorocyclobutane (PFC-C318), all isomers of C$_4$F$_{10}$ (PFC-31-10), hexafluoropropylene (HFP, PFC-1216), all isomers of C$_5$F$_{12}$ (PFC-41-12), all isomers of C$_6$F$_{14}$ (PFC-51-14), PMVE (perfluoromethylvinylether), PEVE (perfluoroethylvinylether), and mixtures thereof.

In one embodiment, the present composition comprises:
a. from about 5 weight percent to about 15 weight percent, HF;
b. from about 30 weight percent to about 80 weight percent fluoroolefin; and
c. from about 5 weight percent to about 70 weight percent extractant.

In certain embodiments, in the process of purifying fluoroolefin from a composition comprising HF and fluoroolefin, the fluoroolefin comprises a fluoropropene. In one embodiment, the fluoroolefin is Z-HFC-1225ye, E-HFC-1225ye, or any combination or mixture of both isomers in any ratio. In another embodiment, the fluoroolefin is HFC-1234yf. In another embodiment, the fluoroolefin is Z-HFC-1234ze, E-HFC-1234ze, or any combination or mixture of both isomers in any ratio.

In certain embodiments, in the composition comprising HF, at least one fluoroolefin, and at least one extractant, the at least one fluoroolefin comprises a fluoropropene. In one embodiment, the fluoroolefin is Z-HFC-1225ye, E-HFC-1225ye, or any combination or mixture of both isomers in any ratio. In another embodiment, the fluoroolefin is HFC-1234yf. In another embodiment, the fluoroolefin is Z-HFC-1234ze, E-HFC-1234ze, or any combination or mixture of both isomers in any ratio.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compositions, Separation Processes and finally Examples.

1. Definitions and Clarification of Terms

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, an extractant is defined as a fluid that preferentially dissolves or extracts one or more chemical compound from a mixture of chemical compounds and is partially to completely immiscible with one or more of the other constituents of the chemical compound mixture. In this way, it is possible to partially to completely transfer one or more preferentially dissolved chemical compounds from the original mixture of chemical compounds to a second phase formed by the extractant. In the liquid-liquid extraction art, the term "solvent" is often used instead of extractant.

As used herein, when a product on any process step is said to be "essentially free of" any substance is meant that the process step produces a compound that contains less than about 100 ppm (weight basis) of the substance. In another embodiment the compound produced contains less than about 10 ppm of the substance. In yet another embodiment the compound produced contains less than about 1 ppm, of the substance.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

2. Compositions

Hydrogen fluoride (HF, anhydrous) is a commercially available chemical or can be produced by methods known in the art.

The term "fluoroolefin" is intended to mean a compound comprising carbon and fluorine and optionally hydrogen that additionally comprises at least one double bond.

In one embodiment, fluoroolefins comprise compounds with 2 to 12 carbon atoms, in another embodiment the fluoroolefins comprise compounds with 3 to 10 carbon atoms, and in yet another embodiment the fluoroolefins comprise compounds with 3 to 7 carbon atoms. Representative fluoroolefins include but are not limited to all compounds as listed in Table 1, Table 2, and Table 3.

The present invention provides fluoroolefins having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)CF_2CF_2C_2F_5$, and $C(CF_3)_2 CF_2C_2F_5$. In one embodiment the fluoroolefins of Formula I, have at least 4 carbon atoms in the molecule. In yet another embodiment, the fluoroolefins of Formula I have at least 5 carbon atoms in the molecule. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |
| F22E | $C_2F_5CH=CHC_2F_5$ | 1,1,1,2,2,5,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF—(CF_3)_2$ | 1,1,1,4,4,5,6,6,6-nonafluoro-5-(trifluoromethyl)hex-2-ene |
| F14sE | $CF_3CH=CHCF(CF_3)—C_2F_5$ | 1,1,1,4,5,5,6,6,6-nonfluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,6,6,6-nonafluoro-5-(trifluoromethyl)hex-3-ene |
| F15E | $CF_3CH=CH(CF_2)_4CF_3$ | 1,1,1,4,4,5,5,6,6,7,7,8,8,8-tetradecafluorooct-2-ene |
| F15iE | $CF_3CH=CH—CF_2CF_2CF(CF_3)_2$ | 1,1,1,4,4,5,5,6,7,7,7-undecafluoro-6-(trifluoromethyl)hept-2-ene |
| F15tE | $CF_3CH=CH—C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF—(CF_3)_2$ | 1,1,1,2,2,5,5,6,7,7,7-undecafluoro-6-(trifluoromethyl)hept-3-ene |
| F24sE | $C_2F_5CH=CHCF(CF_3)—C_2F_5$ | 1,1,1,2,2,5,6,6,7,7,7-undecafluoro-5-(trifluoromethyl)hept-3-ene |

TABLE 1-continued

| Code | Structure | Chemical Name |
|---|---|---|
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH-CF_2C_2F_5$ | 1,1,1,2,2,3,3,6,6,7,7,8,8,8-tetradecafluorooct-4-ene |
| F3i3iE | $(CF_3)_2CFCH=CH-CF(CF_3)_2$ | 1,1,1,2,5,6,6,6-octafluoro-2,5-bis(trifluoromethyl)hex-3-ene |
| F33iE | $C_2F_5CF_2CH=CH-CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH-CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH-C(CF_3)_2C_2F_5$ | 1,1,1,2,2,6,6,7,7,7-decafluoro-5,5-bis(trifluoromethyl)hept-3-ene |
| F34E | $C_2F_5CF_2CH=CH-(CF_2)_3CF_3$ | 1,1,1,2,2,3,3,6,6,7,7,8,8,9,9,9-hexadecafluoronon-4-ene |
| F34iE | $C_2F_5CF_2CH=CH-CF_2CF(CF_3)_2$ | 1,1,1,2,2,3,3,6,6,7,7,8,8,8-tridecafluoro-7-(trifluoromethyl)oct-4-ene |
| F34sE | $C_2F_5CF_2CH=CH-CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH-C(CF_3)_3$ | 1,1,1,5,5,6,6,7,7,7-decafluoro-2,2-bis(trifluoromethyl)hept-3-ene |
| F3i4E | $(CF_3)_2CFCH=CH-(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH-CF_2CF(CF_3)_2$ | 1,1,1,2,5,5,6,6,7,7,7-decafluoro-2,6-bis(trifluoromethyl)hept-3-ene |
| F3i4sE | $(CF_3)_2CFCH=CH-CF(CF_3)C_2F_5$ | 1,1,1,2,5,6,6,7,7,7-decafluoro-2,5-bis(trifluoromethyl)hept-3-ene |
| F3i4tE | $(CF_3)_2CFCH=CH-C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)(CF_2)_2C_2F_5$ | 1,1,1,2,2,5,6,6,7,7,8,8,9,9,9-pentadecafluoro-5-(trifluoromethyl)non-3-ene |
| F26tE | $C_2F_5CH=CHC(CF_3)_2CF_2C_2F_5$ | 1,1,1,2,2,6,6,7,7,8,8,8-dodecafluoro-5,5-bis(trifluoromethyl)oct-3-ene |
| F35E | $C_2F_5CF_2CH=CH-(CF_2)_4CF_3$ | 1,1,1,2,2,3,3,6,6,7,7,8,8,9,9,10,10,10-octadecafluorodec-4-ene |
| F35iE | $C_2F_5CF_2CH=CH-CF_2CF_2CF(CF_3)_2$ | 1,1,1,2,2,3,3,6,6,7,7,8,9,9,9-pentadecafluoro-8-(trifluoromethyl)non-4-ene |
| F35tE | $C_2F_5CF_2CH=CH-C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH-(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH-CF_2CF_2CF(CF_3)_2$ | 1,1,1,2,5,5,6,6,7,8,8,8-dodecafluoro-2,7-bis(trifluoromethyl)oct-3-ene |
| F3i5tE | $(CF_3)_2CFCH=CH-C(CF_3)_2C_2F_5$ | 1,1,1,2,6,6,7,7,7-nonafluoro-2,5,5-tris(trifluoromethyl)hept-3-ene |
| F44E | $CF_3(CF_2)_3CH=CH-(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH-CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH-CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH-C(CF_3)_3$ | 1,1,1,5,5,6,6,7,7,8,8,8-dodecafluoro-2,2,-bis(trifluoromethyl)oct-3-ene |
| F4i4iE | $(CF_3)_2CFCF_2CH=CH-CF_2CF(CF_3)_2$ | 1,1,1,2,3,3,6,6,7,8,8,8-dodecafluoro-2,7-bis(trifluoromethyl)oct-4-ene |
| F4i4sE | $(CF_3)_2CFCF_2CH=CH-CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH-C(CF_3)_3$ | 1,1,1,5,5,6,7,7,7-nonafluoro-2,2,6-tris(trifluoromethyl)hept-3-ene |
| F4s4sE | $C_2F_5CF(CF_3)CH=CH-CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH-C(CF_3)_3$ | 1,1,1,5,6,6,7,7,7-nonafluoro-2,2,5-tris(trifluoromethyl)hept-3-ene |
| F4t4tE | $(CF_3)_3CCH=CH-C(CF_3)_3$ | 1,1,1,6,6,6-hexafluoro-2,2,5,5-tetrakis(trifluoromethyl)hex-3-ene |

Compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$.

Said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include fabricated from stainless steels, in particular of the austenitic type, and the well-known high nickel alloys such as Monel® nickel-copper alloys, Hastelloy® nickel based alloys and Inconel® nickel-chromium alloys.

Alternatively, the reaction may take be conducted in semi-batch mode in which the perfluoroalkyltrihydroolefin reactant is added to the perfluoroalkyl iodide reactant by means of a suitable addition apparatus such as a pump at the reaction temperature.

The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et. al. in *Journal of Fluorine Chemistry*, Vol. 4, pages 261-270 (1974).

Preferred temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C.

Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or may preferably be recovered and purified by distillation prior to the dehydroiodination step.

The dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide.

Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point product and the ease of separation of traces of the solvent from the product during purification. Typically, ethanol or isopropanol are good solvents for the reaction.

Typically, the dehydroiodination reaction may be carried out by addition of one of the reactants (either the basic substance or the trihydroiodoperfluoroalkane) to the other reactant in a suitable reaction vessel. Said reaction may be fabricated from glass, ceramic, or metal and is preferably agitated with an impeller or stirring mechanism.

Temperatures suitable for the dehydroiodination reaction are from about 10° C. to about 100° C., preferably from about 20° C. to about 70° C. The dehydroiodination reaction may be carried out at ambient pressure or at reduced or elevated pressure. Of note are dehydroiodination reactions in which the compound of Formula I is distilled out of the reaction vessel as it is formed.

Alternatively, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), or cyclic polyether compounds known in the art as crown ethers (e.g., 18-crown-6 and 15-crown-5).

Alternatively, the dehydroiodination reaction may be conducted in the absence of solvent by adding the trihydroiodoperfluoroalkane to a solid or liquid basic substance.

Suitable reaction times for the dehydroiodination reactions are from about 15 minutes to about six hours or more depending on the solubility of the reactants. Typically the dehydroiodination reaction is rapid and requires about 30 minutes to about three hours for completion. The compound of formula I may be recovered from the dehydroiodination reaction mixture by phase separation after addition of water, by distillation, or by a combination thereof.

In another embodiment of the present invention, fluoroolefins comprise cyclic unsaturated fluorocarbons (cyclo-[CX=CY(CZW)$_n$—] (Formula II), wherein X, Y, Z, and W are independently selected from H and F, and n is an integer from 2 to 5). In one embodiment the fluoroolefins of Formula II, have at least about 3 carbon atoms in the molecule. In another embodiment, the fluoroolefins of Formula II have at least about 4 carbon atoms in the molecule. In yet another embodiment, the fluoroolefins of Formula II have at least about 5 carbon atoms in the molecule. Representative cyclic fluoroolefins of Formula II are listed in Table 2.

TABLE 2

| Cyclic unsaturated fluorocarbons | Structure | Chemical name |
| --- | --- | --- |
| FC-C1316cc | cyclo-CF$_2$CF$_2$CF=CF— | 1,2,3,3,4,4-hexafluorocyclobutene |
| HFC-C1334cc | cyclo-CF$_2$CF$_2$CH=CH— | 3,3,4,4-tetrafluorocyclobutene |
| HFC-C1436 | cyclo-CF$_2$CF$_2$CF$_2$CH=CH— | 3,3,4,4,5,5,-hexafluorocyclopentene |

TABLE 2-continued

| Cyclic unsaturated fluorocarbons | Structure | Chemical name |
|---|---|---|
| FC-C1418y | cyclo-$CF_2CF=CFCF_2CF_2$— | 1,2,3,3,4,4,5,5-octafluorocyclopentene |
| FC-C151-10y | cyclo-$CF_2CF=CFCF_2CF_2CF_2$— | 1,2,3,3,4,4,5,5,6,6-decafluorocyclohexene |

The compositions of the present invention may comprise a single compound of Formula I or formula II, for example, one of the compounds in Table 1 or Table 2, or may comprise a combination of compounds of Formula I or Formula II.

In another embodiment, fluoroolefins may comprise those compounds listed in Table 3.

TABLE 3

| Name | Structure | Chemical name |
|---|---|---|
| HFC-1114 (TFE) | $CF_2=CF_2$ | tetrafluoroethylene |
| HFC-1216 (HFP) | $CF_3CF=CF_2$ | hexafluoropropene |
| HFC-1225ye | $CF_3CF=CHF$ | 1,2,3,3,3-pentafluoro-1-propene |
| HFC-1225zc | $CF_3CH=CF_2$ | 1,1,3,3,3-pentafluoro-1-propene |
| HFC-1225yc | $CHF_2CF=CF_2$ | 1,1,2,3,3-pentafluoro-1-propene |
| HFC-1234ye | $CHF_2CF=CHF$ | 1,2,3,3-tetrafluoro-1-propene |
| HFC-1234yf | $CF_3CF=CH_2$ | 2,3,3,3-tetrafluoro-1-propene |
| HFC-1234ze | $CF_3CH=CHF$ | 1,3,3,3-tetrafluoro-1-propene |
| HFC-1234yc | $CH_2FCF=CF_2$ | 1,1,2,3-tetrafluoro-1-propene |
| HFC-1234zc | $CHF_2CH=CF_2$ | 1,1,3,3-tetrafluoro-1-propene |
| HFC-1243yf | $CHF_2CF=CH_2$ | 2,3,3-trifluoro-1-propene |
| HFC-1243zf | $CF_3CH=CH_2$ | 3,3,3-trifluoro-1-propene |
| HFC-1243yc | $CH_3CF=CF_2$ | 1,1,2-trifluoro-1-propene |
| HFC-1243zc | $CH_2FCH=CF_2$ | 1,1,3-trifluoro-1-propene |
| HFC-1243ye | $CH_2FCF=CHF$ | 1,2,3-trifluoro-1-propene |
| HFC-1243ze | $CHF_2CH=CHF$ | 1,3,3-trifluoro-1-propene |
| FC-1318my | $CF_3CF=CFCF_3$ | 1,1,1,2,3,4,4,4-octafluoro-2-butene |
| FC-1318cy | $CF_3CF_2CF=CF_2$ | 1,1,2,3,3,4,4,4-octafluoro-1-butene |
| HFC-1327my | $CF_3CF=CHCF_3$ | 1,1,1,2,4,4,4-heptafluoro-2-butene |
| HFC-1327ye | $CHF=CFCF_2CF_3$ | 1,2,3,3,4,4,4-heptafluoro-1-butene |
| HFC-1327py | $CHF_2CF=CFCF_3$ | 1,1,1,2,3,4,4-heptafluoro-2-butene |
| HFC-1327et | $(CF_3)_2C=CHF$ | 1,3,3,3-tetrafluoro-2-(trifluoromethyl)-1-propene |
| HFC-1327cz | $CF_2=CHCF_2CF_3$ | 1,1,3,3,4,4,4-heptafluoro-1-butene |
| HFC-1327cye | $CF_2=CFCHFCF_3$ | 1,1,2,3,4,4,4-heptafluoro-1-butene |
| HFC-1327cyc | $CF_2=CFCF_2CHF_2$ | 1,1,2,3,3,4,4-heptafluoro-1-butene |
| HFC-1336yf | $CF_3CF_2CF=CH_2$ | 2,3,3,4,4,4-hexafluoro-1-butene |
| HFC-1336ze | $CHF=CHCF_2CF_3$ | 1,3,3,4,4,4-hexafluoro-1-butene |
| HFC-1336eye | $CHF=CFCHFCF_3$ | 1,2,3,4,4,4-hexafluoro-1-butene |
| HFC-1336eyc | $CHF=CFCF_2CHF_2$ | 1,2,3,3,4,4-hexafluoro-1-butene |
| HFC-1336pyy | $CHF_2CF=CFCHF_2$ | 1,1,2,3,4,4-hexafluoro-2-butene |
| HFC-1336qy | $CH_2FCF=CFCF_3$ | 1,1,1,2,3,4-hexafluoro-2-butene |
| HFC-1336pz | $CHF_2CH=CFCF_3$ | 1,1,1,2,4,4-hexafluoro-2-butene |
| HFC-1336mzy | $CF_3CH=CFCHF_2$ | 1,1,1,3,4,4-hexafluoro-2-butene |
| HFC-1336qc | $CF_2=CFCF_2CH_2F$ | 1,1,2,3,3,4-hexafluoro-1-butene |
| HFC-1336pe | $CF_2=CFCHFCHF_2$ | 1,1,2,3,4,4-hexafluoro-1-butene |
| HFC-1336ft | $CH_2=C(CF_3)_2$ | 3,3,3-trifluoro-2-(trifluoromethyl)-1-propene |
| HFC-1345qz | $CH_2FCH=CFCF_3$ | 1,1,1,2,4-pentafluoro-2-butene |
| HFC-1345mzy | $CF_3CH=CFCH_2F$ | 1,1,1,3,4-pentafluoro-2-butene |
| HFC-1345fz | $CF_3CF_2CH=CH_2$ | 3,3,4,4,4-pentafluoro-1-butene |
| HFC-1345mzz | $CHF_2CH=CHCF_3$ | 1,1,1,4,4-pentafluoro-2-butene |
| HFC-1345sy | $CH_3CF=CFCF_3$ | 1,1,1,2,3-pentafluoro-2-butene |
| HFC-1345fyc | $CH_2=CFCF_2CHF_2$ | 2,3,3,4,4-pentafluoro-1-butene |
| HFC-1345pyz | $CHF_2CF=CHCHF_2$ | 1,1,2,4,4-pentafluoro-2-butene |
| HFC-1345cyc | $CH_3CF_2CF=CF_2$ | 1,1,2,3,3-pentafluoro-1-propene |
| HFC-1345pyy | $CH_2FCF=CFCHF_2$ | 1,1,2,3,4-pentafluoro-2-butene |
| HFC-1345eyc | $CH_2FCF_2CF=CF_2$ | 1,2,3,3,4-pentafluoro-1-butene |
| HFC-1345ctm | $CF_2=C(CF_3)(CH_3)$ | 1,1,3,3,3-pentafluoro-2-methyl-1-propene |
| HFC-1345ftp | $CH_2=C(CHF_2)(CF_3)$ | 2-(difluoromethyl)-3,3,3-trifluoro-1-propene |
| HFC1345fye | $CH_2=CFCHFCF_3$ | 2,3,4,4,4-pentafluoro-1-butene |
| HFC-1345eyf | $CHF=CFCH_2CF_3$ | 1,2,4,4,4-pentafluoro-1-butene |
| HFC-1345eze | $CHF=CHCHFCF_3$ | 1,3,4,4,4-pentafluoro-1-butene |
| HFC-1345ezc | $CHF=CHCF_2CHF_2$ | 1,3,3,4,4-pentafluoro-1-butene |

TABLE 3-continued

| Name | Structure | Chemical name |
|---|---|---|
| HFC-1345eye | CHF=CFCHFCHF$_2$ | 1,2,3,4,4-pentafluoro-1-butene |
| HFC-1354fzc | CH$_2$=CHCF$_2$CHF$_2$ | 3,3,4,4-tetrafluoro-1-butene |
| HFC-1354ctp | CF$_2$=C(CHF$_2$)(CH$_3$) | 1,1,3,3-tetrafluoro-2-methyl-1-propene |
| HFC-1354etm | CHF=C(CF$_3$)(CH$_3$) | 1,3,3,3-tetrafluoro-2-methyl-1-propene |
| HFC-1354tfp | CH$_2$=C(CHF$_2$)$_2$ | 2-(difluoromethyl)-3,3-difluoro-1-propene |
| HFC-1354my | CF$_3$CF=CHCH$_3$ | 1,1,1,2-tetrafluoro-2-butene |
| HFC-1354mzy | CH$_3$CF=CHCF$_3$ | 1,1,1,3-tetrafluoro-2-butene |
| FC-141-10myy | CF$_3$CF=CFCF$_2$CF$_3$ | 1,1,1,2,3,4,4,5,5,5-decafluoro-2-pentene |
| FC-141-10cy | CF$_2$=CFCF$_2$CF$_2$CF$_3$ | 1,1,2,3,3,4,4,5,5,5-decafluoro-1-pentene |
| HFC-1429mzt | (CF$_3$)$_2$C=CHCF$_3$ | 1,1,1,4,4,4-hexafluoro-2-(trifluoromethyl)-2-butene |
| HFC-1429myz | CF$_3$CF=CHCF$_2$CF$_3$ | 1,1,1,2,4,4,5,5,5-nonafluoro-2-pentene |
| HFC-1429mzy | CF$_3$CH=CFCF$_2$CF$_3$ | 1,1,1,3,4,4,5,5,5-nonafluoro-2-pentene |
| HFC-1429eyc | CHF=CFCF$_2$CF$_2$CF$_3$ | 1,2,3,3,4,4,5,5,5-nonafluoro-1-pentene |
| HFC-1429czc | CF$_2$=CHCF$_2$CF$_2$CF$_3$ | 1,1,3,3,4,4,5,5,5-nonafluoro-1-pentene |
| HFC-1429cycc | CF$_2$=CFCF$_2$CF$_2$CHF$_2$ | 1,1,2,3,3,4,4,5,5-nonafluoro-1-pentene |
| HFC-1429pyy | CHF$_2$CF=CFCF$_2$CF$_3$ | 1,1,2,3,4,4,5,5,5-nonafluoro-2-pentene |
| HFC-1429myyc | CF$_3$CF=CFCF$_2$CHF$_2$ | 1,1,1,2,3,4,4,5,5-nonafluoro-2-pentene |
| HFC-1429myye | CF$_3$CF=CFCHFCF$_3$ | 1,1,1,2,3,4,5,5,5-nonafluoro-2-pentene |
| HFC-1429eyym | CHF=CFCF(CF$_3$)$_2$ | 1,2,3,4,4,4-hexafluoro-3-(trifluoromethyl)-1-butene |
| HFC-1429cyzm | CF$_2$=CFCH(CF$_3$)$_2$ | 1,1,2,4,4,4-hexafluoro-3-(trifluoromethyl)-1-butene |
| HFC-1429mzt | CF$_3$CH=C(CF$_3$)$_2$ | 1,1,1,4,4,4-hexafluoro-2-(trifluoromethyl)-2-butene |
| HFC-1429czym | CF$_2$=CHCF(CF$_3$)$_2$ | 1,1,3,4,4,4-hexafluoro-3-(trifluoromethyl)-1-butene |
| HFC-1438fy | CH$_2$=CFCF$_2$CF$_2$CF$_3$ | 2,3,3,4,4,5,5,5-octafluoro-1-pentene |
| HFC-1438eycc | CHF=CFCF$_2$CF$_2$CHF$_2$ | 1,2,3,3,4,4,5,5-octafluoro-1-pentene |
| HFC-1438ftmc | CH$_2$=C(CF$_3$)CF$_2$CF$_3$ | 3,3,4,4-pentafluoro-2-(trifluoromethyl)-1-butene |
| HFC-1438czzm | CF$_2$=CHCH(CF$_3$)$_2$ | 1,1,4,4,4-pentafluoro-3-(trifluoromethyl)-1-butene |
| HFC-1438ezym | CHF=CHCF(CF$_3$)$_2$ | 1,3,4,4,4-pentafluoro-3-(trifluoromethyl)-1-butene |
| HFC-1438ctmf | CF$_2$=C(CF$_3$)CH$_2$CF$_3$ | 1,1,4,4,4-pentafluoro-2-(trifluoromethyl)-1-butene |
| HFC-1447fzy | (CF$_3$)$_2$CFCH=CH$_2$ | 3,4,4,4-tetrafluoro-3-(trifluoromethyl)-1-butene |
| HFC-1447fz | CF$_3$CF$_2$CF$_2$CH=CH$_2$ | 3,3,4,4,5,5,5-heptafluoro-1-pentene |
| HFC-1447fycc | CH$_2$=CFCF$_2$CF$_2$CHF$_2$ | 2,3,3,4,4,5,5-heptafluoro-1-pentene |
| HFC-1447czcf | CF$_2$=CHCF$_2$CH$_2$CF$_3$ | 1,1,3,3,5,5,5-heptafluoro-1-pentene |
| HFC-1447mytm | CF$_3$CF=C(CF$_3$)(CH$_3$) | 1,1,1,2,4,4,4-heptafluoro-3-methyl-2-butene |
| HFC-1447fyz | CH$_2$=CFCH(CF$_3$)$_2$ | 2,4,4,4-tetrafluoro-3-(trifluoromethyl)-1-butene |
| HFC-1447ezz | CHF=CHCH(CF$_3$)$_2$ | 1,4,4,4-tetrafluoro-3-(trifluoromethyl)-1-butene |
| HFC-1447qzt | CH$_2$FCH=C(CF$_3$)$_2$ | 1,4,4,4-tetrafluoro-2-(trifluoromethyl)-2-butene |
| HFC-1447syt | CH$_3$CF=C(CF$_3$)$_2$ | 2,4,4,4-tetrafluoro-2-(trifluoromethyl)-2-butene |
| HFC-1456szt | (CF$_3$)$_2$C=CHCH$_3$ | 3-(trifluoromethyl)-4,4,4-trifluoro-2-butene |
| HFC-1456szy | CF$_3$CF$_2$CF=CHCH$_3$ | 3,4,4,5,5,5-hexafluoro-2-pentene |
| HFC-1456mstz | CF$_3$C(CH$_3$)=CHCF$_3$ | 1,1,1,4,4,4-hexafluoro-2-methyl-2-butene |
| HFC-1456fzce | CH$_2$=CHCF$_2$CHFCF$_3$ | 3,3,4,5,5,5-hexafluoro-1-pentene |
| HFC-1456ftmf | CH$_2$=C(CF$_3$)CH$_2$CF$_3$ | 4,4,4-trifluoro-2-(trifluoromethyl)-1-butene |
| FC-151-12c | CF$_3$(CF$_2$)$_3$CF=CF$_2$ | 1,1,2,3,3,4,4,5,5,6,6,6-dodecafluoro-1-hexene (or perfluoro-1-hexene) |
| FC-151-12mcy | CF$_3$CF$_2$CF=CFCF$_2$CF$_3$ | 1,1,1,2,2,3,4,5,5,6,6,6-dodecafluoro-3-hexene (or perfluoro-3-hexene) |
| FC-151-12mmtt | (CF$_3$)$_2$C=C(CF$_3$)$_2$ | 1,1,1,4,4,4-hexafluoro-2,3-bis(trifluoromethyl)-2-butene |
| FC-151-12mmzz | (CF$_3$)$_2$CFCF=CFCF$_3$ | 1,1,1,2,3,4,5,5,5-nonafluoro-4-(trifluoromethyl)-2-pentene |
| HFC-152-11mmtz | (CF$_3$)$_2$C=CHC$_2$F$_5$ | 1,1,1,4,4,5,5,5-octafluoro-2-(trifluoromethyl)-2-pentene |
| HFC-152-11mmyyz | (CF$_3$)$_2$CFCF=CHCF$_3$ | 1,1,1,3,4,5,5,5-octafluoro-4-(trifluoromethyl)-2-pentene |
| PFBE (or HFC-1549fz) | CF$_3$CF$_2$CF$_2$CF$_2$CH=CH$_2$ | 3,3,4,4,5,5,6,6,6-nonafluoro-1-hexene (or perfluorobutylethylene) |
| HFC-1549fztmm | CH$_2$=CHC(CF$_3$)$_3$ | 4,4,4-trifluoro-3,3-bis(trifluoromethyl)-1-butene |
| HFC-1549mmtts | (CF$_3$)$_2$C=C(CH$_3$)(CF$_3$) | 1,1,1,4,4,4-hexafluoro-3-methyl-2-(trifluoromethyl)-2-butene |
| HFC-1549fycz | CH$_2$=CFCF$_2$CH(CF$_3$)$_2$ | 2,3,3,5,5,5-hexafluoro-4-(trifluoromethyl)-1-pentene |

TABLE 3-continued

| Name | Structure | Chemical name |
|---|---|---|
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFC-162-13mzy | $CF_3CH=CFCF_2CF_2C_2F_5$ | 1,1,1,3,4,4,5,5,6,6,7,7,7-tridecafluoro-2-heptene |
| HFC162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |

The compounds listed in Table 2 and Table 3 are available commercially or may be prepared by processes known in the art or as described herein.

1,1,1,4,4-pentafluoro-2-butene may be prepared from 1,1,1,2,4,4-hexafluorobutane ($CHF_2CH_2CHFCF_3$) by dehydrofluorination over solid KOH in the vapor phase at room temperature. The synthesis of 1,1,1,2,4,4-hexafluorobutane is described in U.S. Pat. No. 6,066,768, incorporated herein by reference.

1,1,1,4,4,4-hexafluoro-2-butene may be prepared from 1,1,1,4,4,4-hexafluoro-2-iodobutane ($CF_3CHICH_2CF_3$) by reaction with KOH using a phase transfer catalyst at about 60° C. The synthesis of 1,1,1,4,4,4-hexafluoro-2-iodobutane may be carried out by reaction of perfluoromethyl iodide ($CF_3I$) and 3,3,3-trifluoropropene ($CF_3CH=CH_2$) at about 200° C. under autogenous pressure for about 8 hours.

3,4,4,5,5,5-hexafluoro-2-pentene may be prepared by dehydrofluorination of 1,1,1,2,2,3,3-heptafluoropentane ($CF_3CF_2CF_2CH_2CH_3$) using solid KOH or over a carbon catalyst at 200-300° C. 1,1,1,2,2,3,3-heptafluoropentane may be prepared by hydrogenation of 3,3,4,4,5,5,5-heptafluoro-1-pentene ($CF_3CF_2CF_2CH=CH_2$).

1,1,1,2,3,4-hexafluoro-2-butene may be prepared by dehydrofluorination of 1,1,1,2,3,3,4-heptafluorobutane ($CH_2FCF_2CHFCF_3$) using solid KOH.

1,1,1,2,4,4-hexafluoro-2-butene may be prepared by dehydrofluorination of 1,1,1,2,2,4,4-heptafluorobutane ($CHF_2CH_2CF_2CF_3$) using solid KOH.

1,1,1,3,4,4-hexafluoro2-butene may be prepared by dehydrofluorination of 1,1,1,3,3,4,4-heptafluorobutane ($CF_3CH_2CF_2CHF_2$) using solid KOH.

1,1,1,2,4-pentafluoro-2-butene may be prepared by dehydrofluorination of 1,1,1,2,2,3-hexafluorobutane ($CH_2FCH_2CF_2CF_3$) using solid KOH.

1,1,1,3,4-pentafluoro-2-butene may be prepared by dehydrofluorination of 1,1,1,3,3,4-hexafluorobutane ($CF_3CH_2CF_2CH_2F$) using solid KOH.

1,1,1,3-tetrafluoro-2-butene may be prepared by reacting 1,1,1,3,3-pentafluorobutane ($CF_3CH_2CF_2CH_3$) with aqueous KOH at 120° C.

1,1,1,4,4,5,5,5-octafluoro-2-pentene may be prepared from ($CF_3CHICH_2CF_2CF_3$) by reaction with KOH using a phase transfer catalyst at about 60° C. The synthesis of 4-iodo-1,1,1,2,2,5,5,5-octafluoropentane may be carried out by reaction of perfluoroethyliodide ($CF_3CF_2I$) and 3,3,3-trifluoropropene at about 200° C. under autogenous pressure for about 8 hours.

1,1,1,2,2,5,5,6,6,6-decafluoro-3-hexene may be prepared from 1,1,1,2,2,5,5,6,6,6-decafluoro-3-iodohexane ($CF_3CF_2CHICH_2CF_2CF_3$) by reaction with KOH using a phase transfer catalyst at about 60° C. The synthesis of 1,1,2,2,5,5,6,6,6-decafluoro-3-iodohexane may be carried out by reaction of perfluoroethyliodide ($CF_3CF_2I$) and 3,3,4,4,4-pentafluoro-1-butene ($CF_3CF_2CH=CH_2$) at about 200° C. under autogenous pressure for about 8 hours.

1,1,1,4,5,5,5-heptafluoro-4-(trifluoromethyl)-2-pentene may be prepared by the dehydrofluorination of 1,1,1,2,5,5,5-heptafluoro-4-iodo-2-(trifluoromethyl)-pentane ($CF_3CHICH_2CF(CF_3)_2$) with KOH in isopropanol. $CF_3CHICH_2CF(CF_3)_2$ is made from reaction of $(CF_3)_2CFI$ with $CF_3CH=CH_2$ at high temperature, such as about 200° C.

1,1,1,4,4,5,5,6,6,6-decafluoro-2-hexene may be prepared by the reaction of 1,1,1,4,4,4-hexafluoro-2-butene ($CF_3CH=CHCF_3$) with tetrafluoroethylene ($CF_2=CF_2$) and antimony pentafluoride ($SbF_5$).

2,3,3,4,4-pentafluoro-1-butene may be prepared by dehydrofluorination of 1,1,2,2,3,3-hexafluorobutane over fluorided alumina at elevated temperature.

2,3,3,4,4,5,5,5-ocatafluoro-1-pentene may be prepared by dehydrofluorination of 2,2,3,3,4,4,5,5,5-nonafluoropentane over solid KOH.

1,2,3,3,4,4,5,5-octafluoro-1-pentene may be prepared by dehydrofluorination of 2,2,3,3,4,4,5,5,5-nonafluoropentane over fluorided alumina at elevated temperature.

Many of the compounds of Formula I, Formula II, Table 1, Table 2, and Table 3 exist as different configurational isomers or stereoisomers. When the specific isomer is not designated, the present invention is intended to include all single configurational isomers, single stereoisomers, or any combination thereof. For instance, F11E is meant to represent the E-isomer, Z-isomer, or any combination or mixture of both isomers in any ratio. As another example, HFC-1225ye is meant to represent the E-isomer, Z-isomer, or any combination or mixture of both isomers in any ratio.

In certain embodiments, in the composition comprising HF, at least one fluoroolefin, and at least one extractant, the at least one fluoroolefin comprises a fluoropropene. In one embodiment, the fluoroolefin is Z-HFC-1225ye, E-HFC-1225ye, or any combination or mixture of both isomers in any ratio. In another embodiment, the fluoroolefin is HFC-1234yf. In another embodiment, the fluoroolefin is Z-HFC-1234ze, E-HFC-1234ze, or any combination or mixture of both isomers in any ratio.

In one embodiment, the extractant may be any compound that would be effective in separation of fluoroolefins from mixtures comprising HF and fluoroolefin in an extraction process. In another embodiment, extractants may be selected from the group consisting of hydrocarbons, chlorocarbons, chlorofluorocarbons, hydrofluorocarbons, hydrochlorofluorocarbons, perfluorocarbons, and perfluorinated ethers.

In one embodiment, hydrocarbon extractants comprise compounds containing 2 to 12 carbon atoms and hydrogen. Hydrocarbon extractants may be linear, branched, cyclic, saturated or unsaturated compounds. Representative hydrocarbon extractants include but are not limited to ethane, ethylene, n-propane propylene, n-butane, isobutane, cyclobutane, 1-butene, 2-butene (cis and trans), n-pentane, isopentane (2-methylbutane), neopentane (2,2-dimethylpropane), cyclopentane, 1-pentene, 2-pentene (cis and trans), cyclopentene, n-hexane, cyclohexane, 2-methylpentane, 3-methylpentane, 1-hexene, 2-hexene (cis and trans), 3-hexene (cis and trans), neohexane (2,2-dimethylbutane), neohexene (3,3-dimethyl-1-butene), 2,2-dimethylbutane, 2,3-dimethylbutane, 2,3-dimethyl-2-butene, 2,3-dimethyl-1-butene, 3,3-dimethyl-1-butene, n-heptane, 1-heptene, 2-heptene (cis and trans), 3-heptene (cis and trans), cycloheptene, octane (all isomers), nonane (all isomers), decane (all isomers), undecane (all isomers), dodecane (all isomers), benzene, toluene, and mixtures thereof.

In another embodiment, chlorocarbon extractants comprise compounds with carbon, chlorine and optionally hydrogen. Representative chlorocarbons include but are not limited to tetrachloroethylene, trichloroethylene, 1,1-dichloroethylene, 1,2-dichloroethylene, carbon tetrachloride (tetrachloromethane), chloroform (trichloromethane), methylene chloride (dichloromethane), 1,1,2,2-tetrachloroethane, 1,1,1,2-tetrachloroethane, 1,1,2-trichloroethane, 1,1,1-trichloroethane, 1,1,1,3,3,3-hexachloropropane and mixtures thereof.

In another embodiment, chlorofluorocarbon (CFC) extractants comprise compounds with carbon, chlorine and fluorine. Representative CFCs include but are not limited to dichlorodifluoromethane (CFC-12), fluorotrichloromethane (CFC-11), fluoropentachloroethane (CFC-111), 1,2-difluoro-1,1,2,2-tetrachloroethane (CFC-112), 1,1-difluoro-1,2,2,2-tetrachloroethane (CFC-112a), 1,1,2-trichloro-1,2,2-trifluoroethane (CFC-113), 1,1,1-trichloro-2,2,2-trifluoroethane (CFC-113a), 1,2-dichloro-1,1,2,2-tetrafluoroethane (CFC-114), 1,1-dichloro-1,2,2,2-tetrafluoroethane (CFC-114a), chloropentafluoroethane (CFC-115), 1,1,1,2,3-pentafluoro-2,3,3-trichloropropane (CFC-215bb), 2,2-dichloro-1,1,1,3,3,3-hexafluoropropane (CFC-216aa), 2,3-dichloro-1,1,1,2,3,3-hexafluoropropane (CFC-216ba), and 2-chloro-1,1,1,2,3,3,3-heptafluoropropane (CFC-217ba), and mixtures thereof.

In another embodiment, hydrochlorofluorocarbon (HCFC) extractants comprise compounds with carbon, chlorine, fluorine and hydrogen. Representative HCFCs include but are not limited to dichlorofluoromethane (HCFC-21), 1,1,2-trichloro-2,2-difluoroethane (HCFC-122), 2,2-dichloro-1,1,1-trifluoroethane (HCFC-123), 1,2-dichloro-1,1,1-trifluoroethane (HCFC-123a), 2-chloro-1,1,1,2-tetrafluoroethane (HCFC-124), 1-chloro-1,1,2,2-tetrafluoroethane (HCFC-124a), 1-chloro-1,2,2-trifluoroethane (HCFC-133), 2-chloro-1,1,1-trifluoroethane (HCFC-133a), 1,1-dichloro-2-fluoroethane (HCFC-141a), 1,1-dichloro-1-fluoroethane (HCFC-141b), 1-chloro-1,2-difluoroethane (HCFC-142a), 1-chloro-1,1-difluoroethane (HCFC-142b), and mixtures thereof.

Hydrofluorocarbon (HFC) extractants comprise compounds that contain carbon, hydrogen and fluorine, and may be saturated or unsaturated (thus including fluoroolefins). Representative HFCs include but are not limited to 1,1,1,2,2,3,4,5,5,6,6,7,7,7-tetradecafluoroheptane (HFC-63-14mcee), 3,3,4,4,5,5,6,6,6-nonafluoro-1-hexene, 1,1,1,2,2,4,5,5,6,6,7,7-tridecafluoro-3-heptene (HFC-162-13mczy), fluorobenzene, 1,1,1,2,2,3,4,5,5,6,6,7,7,7-tetradecafluoroheptane (HFC-63-14mcee), 3,3,4,4,5,5,6,6,6-nonafluoro-1-hexene, HFC-162-13mczy, 1,2,3,3,3-pentafluoro-1-propene (HFC-1225ye), 1,1,3,3,3-pentafluoro-1-propene (HFC-1225zc), 1,3,3,3-tetrafluoro-1-propene (HFC-1234ze), 2,3,3,3-tetrafluoro-1-propene (HFC-1234yf, 3,3,3-trifluoro-1-propene (HFC-1243zf), 1,1,1,2,4,4,5,5,5-nonafluoro-2-pentene (HFC-1429myz), 1,1,1,3,4,4,5,5,5-nonafluoro-2-pentene (HFC-1429mzy), 1,1,1,4,4,4-hexafluoro-2-butene (F11E), 1,1,1,4,4,5,5,5-octafluoro-2-pentene (F12E), 1,1,1,2,2,5,5,6,6,7,7,8,8,8-tetradecafluoro-3-octene (F24E), 1,1,1,2,2,3,3,6,6,7,7,8,8,8-tetradecafluoro-4-octene (F33E), and mixtures thereof.

Perfluorocarbon (PFC) extractants comprise compounds with carbon and fluorine only. Representative PFCs include but are not limited to octafluoropropane (PFC-218), octafluorocyclobutane (PFC-C318), all isomers of $C_4F_{10}$ (PFC-31-10), hexafluoropropylene (HFP, PFC-1216), all isomers of $C_5F_{12}$ (PFC-41-12), all isomers of $C_6F_{14}$ (PFC-51-14) and mixtures thereof.

Perfluorinated ether extractants include but are not limited to PMVE (perfluoromethylvinyl ether) and PEVE (perfluoroethylvinyl ether.

Extractants as described above are available commercially or may be produced by methods known in the art.

The weight ratio of the HF, fluoroolefin, and extractant in the composition present in the extractor will depend upon the means of producing the composition and the efficiency of the extraction. In one embodiment, the HF may be from about 5 weight percent to about 15 weight percent of the composition; the fluoroolefin may be from about 30 weight percent to about 80 weight percent and the extractant may be from about 5 to about 70 weight percent.

In another embodiment, the HF may be from about 5 weight percent to about 15 weight percent; the fluoroolefin may be from about 40 weight percent to about 75 weight percent; and the extractant may be from about 10 weight percent to about 60 weight percent.

In one embodiment, the compositions comprising HF, fluoroolefin and extractant may be prepared by any convenient method to combine the desired amounts of the individual components. One method is to weigh the desired component amounts and thereafter combine the components in an appropriate vessel. Agitation may be used, if desired.

Alternatively, the compositions comprising HF and fluoroolefin may be prepared by feeding the effluent from a dehydrofluorination reactor that contains HF and fluoroolefin to the extractor. The extractant may be added at a separate feed point such that the composition comprising HF, fluoroolefin, and extractant is formed directly in the extractor. Mixing may be accomplished by any usual means, or mixing may be accomplished by feeding the lower density phase (HF/fluoroolefin phase or extractant phase) to the extractor at a point lower than the higher density phase such that the lower density phase will rise through the higher density phase resulting in a mixed composition.

The compositions as described above may be representative of the contents of the extractor in the separation process to be described below. The composition may be different at different points in the extractor.

3. Separation Processes

In one embodiment, the process for separating fluoroolefin from a composition of HF and fluoroolefin may be accomplished by feeding a composition comprising HF and fluoroolefin to an extractor. The composition comprising HF and fluoroolefin may be prepared by any usual method. In one embodiment a composition comprising reactor effluent from a dehydrofluorination reactor will contain a 50/50 mole percent composition of HF and fluoroolefin (eg., 13.2 weight percent HF and 86.8 weight percent fluoroolefin for HF/HFC-1225ye product of dehydrofluorination).

In certain embodiments, in the process of purifying fluoroolefin from a composition comprising HF and fluoroolefin, the fluoroolefin comprises a fluoropropene. In one embodiment, the fluoroolefin is Z-HFC-1225ye, E-HFC-1225ye, or any combination or mixture of both isomers in any ratio. In another embodiment, the fluoroolefin is HFC-1234yf. In another embodiment, the fluoroolefin is Z-HFC-1234ze, E-HFC-1234ze, or any combination or mixture of both isomers in any ratio.

In one embodiment, the process for separating fluoroolefin from a mixture of HF and fluoroolefin comprises feeding the composition comprising HF and fluoroolefin and a composition comprising extractant to an extractor. In one embodiment, the extractor may be any conventional liquid-liquid extraction device, for example a static mixer, a stirred vessel, a mixer/settler, a rotary-disc extractor, an extractor with centrifugation or a column with perforated plates or packing.

In one embodiment, the extractor may operate countercurrently, meaning that the extractant and the composition comprising HF and fluoroolefin flow in opposite directions. In another embodiment, the extractor may operate co-currently, meaning that the extractant and the composition comprising HF and fluoroolefin flow in the same direction.

In one embodiment, the extraction may be carried out in a continuous manner. In another embodiment, the extraction may be carried out in a batch-wise manner.

In some embodiments, the temperature at which the extraction may be carried out depends upon the extractant being used and the fluoroolefin product. In general the lower the boiling point of the extractant the lower the operating temperature and/or the higher the operating pressure that may be required to maintain the composition comprising HF, fluoroolefin and extractant in the liquid state. In one embodiment, the extractor may typically be operated from about $-50°$ C. to about $150°$ C. In another embodiment the extractor may be operated from about $-25°$ C. to about $100°$ C. In yet another embodiment the extractor may be operated from about $-15°$ C. to about $40°$ C.

In one embodiment, the extractor may typically be operated from about 14.7 psia (101.3 kPa) to about 300 psia (2069 kPa). In another embodiment, the extractor may be operated from about 30 psia (206.9 kPa) to about 200 psia (1379 kPa). In one other embodiment the extractor may be operated from about 50 psia (345 kPa) to about 150 psia (1034 kPa). In yet another embodiment, pressure in the extractor may be adjusted by addition of an inert gas. Any gaseous substance, which does not react substantially under the extraction conditions, such as nitrogen, hydrogen chloride, argon or a mixture thereof, may be used as an inert gas.

In one embodiment, the HF/fluoroolefin composition may be of higher density than the extractant, thus the extractant may be fed to a point in the extractor below the feed point of the HF/fluoroolefin composition (as illustrated in FIG. 1). In another embodiment, the HF/fluoroolefin composition may be of lower density than the extractant, thus the extractant may be fed to a point in the extractor above the feed point of the HF/fluoroolefin composition (as illustrated in FIG. 2).

Figure 2:
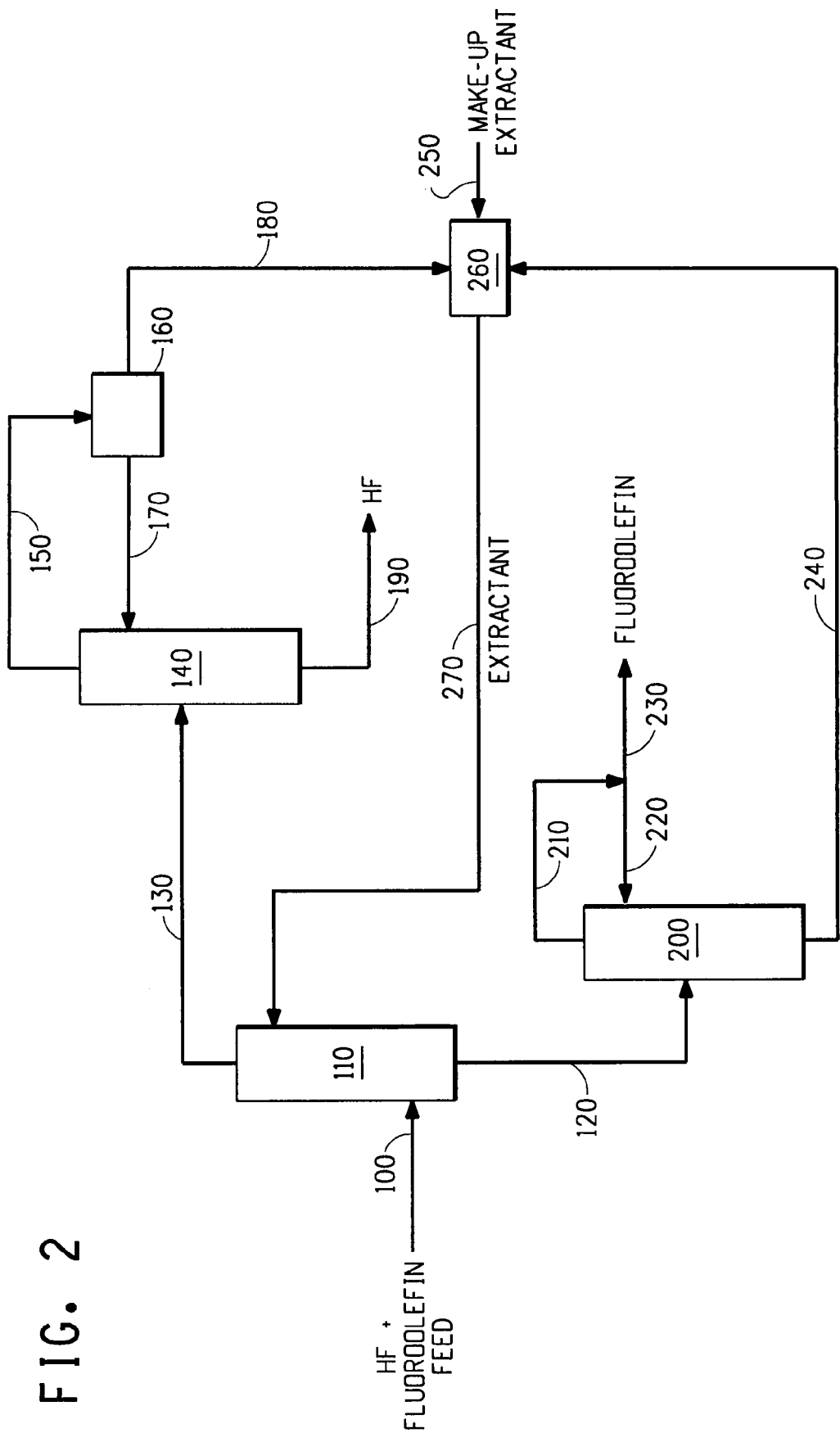
FIG. 2 includes an illustration of a process to separate fluoroolefin from a composition comprising HF and fluoroolefin by liquid-liquid extraction wherein the extractant has a higher density than the composition comprising HF and fluoroolefin.

In certain embodiments (e.g., as illustrated in FIG. 1 and FIG. 2), extractant-rich phase may be removed from the extractor as an extract, comprising extractant and fluoroolefin. The extract may be fed to an extractant recovery column for the recovery of fluoroolefin product essentially free of extractant. In one embodiment, the fluoroolefin is taken off the top of the extractant recovery column. The fluoroolefin product may still contain some minor amount of HF and extractant, which can be removed by any conventional method known in the art, such as aqueous (e.g. caustic) scrubbing or non-aqueous (e.g. alumina, active charcoal or zeolite bed) methods.

In one embodiment, the extractant is removed from the bottom of the extractant recovery column and may be recycled back to the extractor.

In one embodiment, the composition exiting the top of the extractant recovery column comprising fluoroolefin may be condensed using conventional reflux condensers. At least a portion of this condensed stream may be returned to the top of the column as reflux. The ratio of the condensed material, which is returned to the top of the extract recovery column as reflux, to the material removed from the top of the extract recovery column is commonly referred to as the reflux ratio.

The specific conditions, which may be used for operating the extractant recovery column depend upon a number of parameters, such as the physical properties of the extractant used, the diameter of the distillation column, feed points, and the number of separation stages in the column, among others.

The pressures and temperatures required in the extractant recovery column to provide the separations desired will vary depending upon the fluoroolefin being recovered and the extractant being used as well. In one embodiment the extractant recovery column may be operated at a pressure range from about 14.7 psia (101.3 kPa) to about 300 psia (2068.5 kPa) with a top temperature range from about $-50°$ C. to about $100°$ C. and a bottom temperature range from about $50°$ C. to about $250°$ C. In another embodiment the extractant recovery column may be operated from about 50 psia (345 kPa) to about 150 psia (1034 kPa) with a top temperature of about $30°$ C. to about $75°$ C. and a bottom temperature from about $75°$ C. to about $175°$ C.

An HF-rich phase may be removed from the extractor as a raffinate, comprising HF with minor amounts of extractant and fluoroolefin. This recovered HF may be used as is in any usual manner of using HF (e.g. other chemical manufacturing processes). Alternatively, the raffinate may be fed to a raffinate stripping column for the recovery of HF product essentially free of fluoroolefin and extractant. In one embodiment, the HF product is taken off the bottom of the raffinate stripping column. Such HF product may be used in any manner for which HF is found useful. For instance, HF is useful in fluorination of hydrocarbons or chlorocarbons to produce hydrochlorofluorocarbons or hydrofluorocarbons.

In one embodiment, a second extractant-rich phase with minor amounts of HF and fluoroolefin may be removed from the top of the raffinate stripping column. The second extractant-rich phase may be further purified using a decanter that allows phase separation of extractant and HF. In the decanter, the second extractant-rich phase separates into the decanter extractant-rich phase and the decanter HF-rich phase with the lower density phase being the top phase and the higher density phase being the bottom phase. The decanter extractant-rich phase may be recycled back to the extractor while the decanter HF-rich phase may return to the raffinate stripping column as reflux. Residual fluoroolefin present in the second extractant-rich phase will return to the extractor with the extractant.

In one embodiment the raffinate stripping column may be operated at a pressure range from about 14.7 psia (101.3 kPa) to about 100 psia (689.5 kPa) with a top temperature range from about −50° C. to about 90° C. and a bottom temperature range from about 20° C. to about 100° C. In another embodiment the extractant recovery column may be operated from about 50 psia (345 kPa) to about 75 psia (517 kPa) with a top temperature of about 50° C. to about 70° C. and a bottom temperature from about 50° C. to about 70° C.

In one embodiment, as may be seen in the above description, extractant may be recycled to the extractor from both the extractant recovery column and the raffinate stripping column. Even so, there may be a need to provide make-up flow of the extractant to maintain the optimal feed of extractant to the extractor due to common process losses. In one embodiment, the recycle from the extractant recovery column, raffinate stripping column and any required make-up extractant may be fed to a common mixer prior to the feed line to the extractor.

Referring to FIG. 1, the process may be described as follows. The composition comprising HF and fluoroolefin (100) is fed to the extractor (110). The extractant (270) is also fed to the extractor. In general, the lower density composition is fed to a lower point in the extractor to encourage mixing. The raffinate (130) is taken out of the bottom of the extractor to a raffinate stripping column (140). The top stream from the raffinate stripping column (150) is condensed, cooled and fed to a decanter (160) in which tow liquid phases are formed. The HF rich phase (170) from the decanter is sent back to the raffinate stripping column (140) as reflux. The extractant rich phase from the decanter (180) is recycled back to the extractor (110) via a mixer (260). The bottom stream from the raffinate stripping column (190) is recovered as HF essentially free of fluoroolefin and extractant.

The extract (120) from the extractor (110) is fed to an extractant recovery column (200). The extractant recovery column bottom (240), containing essentially all of the extraction in the column feed, is recycled back to the extractor via the mixer (260). The top stream from the extractant recovery column (210) is partially or completely condensed with a portion of condensate returned to the extractant recovery column as reflux (220). The remainder of the stream (210) is recovered as the fluoroolefin product (230), essentially free of extractant.

Referring to FIG. 2, the process may be described as follows. The composition comprising HF and fluoroolefin (100) is fed to the extractor (110). The extractant (270) is also fed to the extractor. The raffinate (130) is taken off the top of the extractor to a raffinate stripping column (140). The top stream from the raffinate stripping column (150) is condensed, cooled and fed to a decanter (160) in which two liquid phases are formed. The extractant rich phase from the decanter (180) is recycled back to the extractor via a mixer (260). The HF rich phase from the decanter (170) is recycled back to the raffinate stripping column as reflux. The bottom stream of the raffinate stripping column (190) is removed as HF essentially free of fluoroolefin and extractant.

The extract (120) from the bottom of the extractor is fed to an extractant recovery column (200). The bottom of the extractant recovery column (240) is recycled back to the extractor via the mixer (260). The top stream from the extractant recovery column (210) is partially or completely condensed with a portion of condensate returned to the extractant recovery column as reflux (220). The remainder of the stream (210) is recovered as the fluoroolefin product (230), essentially free of extractant.

The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

While not illustrated in the figures, it is understood that certain pieces of process equipment may be used in the processes described herein, for optimization. For instance, pumps, heat exchangers, such as heaters or coolers, or other conventional equipment may be used where appropriate. As an example, it is desirable to have the feed to a distillation column at the same temperature as the point in the column that it is fed. Therefore, heating or cooling of the process stream may be necessary to match the temperature.

EXAMPLES

The concepts described herein will be further described in the following examples, which do not limit the scope of the invention described in the claims.

Example 1

HFC-1225zc (1,1,1,3,3-pentafluoropropene) and HF form an azeotrope as disclosed in U.S. Patent Application Publication No. 2006/0116538 A1. Therefore, separation of HF from HFC-1225zc is not possible by conventional distillation. Example 1 demonstrates that HFC-1225zc may be separated from HF by liquid-liquid extraction using n-hexane as the extractant. A composition comprising 50/50 mole percent HF and HFC-1225zc is fed to the top of an extractor at 1000 lbs/hour (454 kg/hour). N-hexane (extractant) is fed to the bottom of the extractor at 500 lbs/hour (227 kg/hour). The data in Table 4 were calculated using measured thermodynamic properties.

TABLE 4

| Component or variable | HF/HFC-1225zc feed (100) | Extract (120) | Raffinate (130) | HFC-1225zc product (230) | HF product (190) |
|---|---|---|---|---|---|
| HF, wt % | 13.2 | 0.44 | 98.0 | 0.69 | 100 |
| HFC-1225zc, wt % | 86.8 | 63.3 | 0.03 | 99.3 | 1 ppm |
| n-hexane, wt % | 0 | 36.3 | 1.97 | 1 ppm | 6 ppm |
| Temp, ° C. | 30.0 | 30.0 | 30.0 | 16.4 | 67.2 |
| Pres, psia (kPa) | 164.7 (1136) | 94.7 (653) | 94.7 (653) | 64.7 (446) | 65.7 (453.0) |

The above data is calculated for an extractor with 6 theoretical stages operating at a temperature of 30° C. The extractant recovery column has 20 theoretical stages (the extract is fed on the $8^{th}$ stage from the bottom), operating at a top pressure of 50 psig and a reflux flow of 1300 lb/hour. The raffinate stripping column has 5 theoretical stages (raffinate fed on the second stage from the bottom), operating at a top pressure of 50 psig and a reflux flow of 75 lb/hour. The decanter operates at a temperature of 0° C.

Example 2

Z-HFC-1225ye (Z-1,1,1,2,3-pentafluoropropene) and HF form an azeotrope as disclosed in U.S. Patent Application Publication No. 2007/0100174 A1. Therefore, separation of HF from Z-HFC-1225ye is not possible by conventional distillation. Example 2 demonstrates that Z-HFC-1225ye may be separated from HF by liquid-liquid extraction using 1,1,2-trichloro-1,2,2-trifluoroethane (CFC-113) as the extractant. A composition comprising 50/50 mole percent HF and Z-HFC-1225ye is fed to the bottom of an extractor at a rate of 1000 lbs/hour (454 kg/hour). CFC-113 (extractant) is fed to the bottom of the extractor at a rate of 800 lbs/hour (363 kg/hour). The data in Table 5 were calculated using measured thermodynamic properties.

The above data is calculated for an extractor with 6 theoretical stages operating at a temperature of 25° C. The extractant recovery column has 20 theoretical stages, the extract is fed on the $5^{th}$ stage from the bottom, and the column operates with a top pressure of 70 psig with 900 lbs/hour reflux. The raffinate stripping column has 5 theoretical stages, the raffinate is fed to the second stage from the top, and the column operates with a top pressure of 50 psig. The decanter operates at a temperature of 30° C.

Example 3

HFP (hexafluoropropene or PFC-1216) and HF form an azeotrope as disclosed in U.S. Pat. No. 6,407,297. Therefore, separation of HF from HFP is not possible by conventional distillation. Example 3 demonstrates that HFP may be separated from HF by liquid-liquid extraction using tetrachloroethylene (perchloroethylene or PCE) as the extractant. A composition comprising 50/50 mole percent HF and HFP is fed to the bottom of an extractor at a rate of 1000 lbs/hour (454 kg/hour). PCE (extractant) is fed to the top of the extractor at

TABLE 5

| Component or variable | HF/Z-HFC-1225ye feed (100) | Extract (120) | Raffinate (130) | Z-HFC-1225ye product (230) | HF product (190) |
|---|---|---|---|---|---|
| HF, wt % | 13.2 | 0.7 | 92.1 | 1.3 | 100 |
| Z-HFC-1225ye, wt % | 86.8 | 52.0 | 200 ppm | 98.7 | <1 ppm |
| CFC-113, wt % | 0 | 47.3 | 7.9 | 10 ppm | 5 ppm |
| Temp, ° C. | 30.0 | 25.0 | 25.0 | 25.2 | 67.2 |
| Pres, psia (kPa) | 164.7 (1135.6) | 84.7 (584.0) | 84.7 (584.0) | 84.7 (584.0) | 65.7 (453) | a rate of 800 lbs/hour (363 kg/hour). The data in Table 6 were calculated using measured thermodynamic properties.

TABLE 6

| Component or variable | HF/HFP feed (100) | Extract (120) | Raffinate (130) | HFP product (230) | HF product (190) |
|---|---|---|---|---|---|
| HF, wt % | 11.8 | 0.35 | 97.3 | 0.66 | 100 |
| HFP, wt % | 88.2 | 52.3 | 1.6 | 99.34 | <1 ppm |
| PCE, wt % | 0 | 47.3 | 1.1 | <1 ppm | 10 ppm |
| Temp, ° C. | 30.0 | 30.0 | 30.0 | −11.0 | 95.4 |
| Pres, psia (kPa) | 164.7 (1135.6) | 144.7 (998) | 144.7 (998) | 34.7 (239) | 135.7 (936) |

The above data is calculated for an extractor with 6 theoretical stages operating at a temperature of 30° C. and pressure of 130 psig. The extractant recovery column has 10 theoretical stages, the extract is fed in the middle of the column, and the column operates with a top pressure of 20 psig with 300 lbs/hour reflux. The raffinate stripping column has 10 theoretical stages, the raffinate is fed to the second stage from the top, and the column operates with a top pressure of 120 psig. The decanter operates at a temperature of 30° C.

Example 4

It is known that tetrafluoroethylene (PFC-1114 or TFE) and HF form an azeotrope. Therefore, separation of HF from TFE is not possible by conventional distillation. Example 4 demonstrates that TFE may be separated from HF by liquid-liquid extraction using octafluoropropane (PFC-218) as the extractant. A composition comprising 50/50 mole percent HF and TFE is fed to the bottom of an extractor at a rate of 1000 lbs/hour (454 kg/hour). PFC-218 (extractant) is fed to the top of the extractor at a rate of 200 lbs/hour (90.7 kg/hour). The data in Table 7 were calculated using measured thermodynamic properties.

Example 5

HFC-1234yf (2,3,3,3-tetrafluoro-1-propene) and HF form an azeotrope as disclosed in U.S. Patent Application Publication No. 2007/0100175 A1. Therefore, separation of HF from HFC-1234yf is not possible by conventional distillation. Example 5 demonstrates that HFC-1234yf may be separated from HF by liquid-liquid extraction using Z-HFC-1225ye (Z-1,2,3,3,3-pentafluoro-1-propene) as the extractant. A composition comprising 50/50 mole percent HF and HFC-1234yf is fed to the bottom of an extractor at a rate of 1000 lbs/hour (454 kg/hour). Z-HFC-1225ye (extractant) is fed to the top of the extractor at a rate of 1000 lbs/hour (454 kg/hour). The data in Table 8 were calculated using measured thermodynamic properties.

TABLE 7

| Component or variable | HF/TFE feed (100) | Extract (120) | Raffinate (130) | TFE product (230) | HF product (190) |
|---|---|---|---|---|---|
| HF, wt % | 16.7 | 0.93 | 82.3 | 1.1 | 100 |
| TFE, wt % | 83.3 | 82.1 | 3.3 | 98.9 | <1 ppm |
| PFC-218, wt % | 0 | 17.0 | 14.4 | 10 ppm | <1 ppm |
| Temp, ° C. | −30.0 | −40.0 | −40.0 | −32.9 | 67.2 |
| Pres, psia (kPa) | 164.7 (1135.6) | 104.7 (722) | 104.7 (722) | 94.7 (653) | 65.7 (453) |

TABLE 8

| Component or variable | HF/HFC-1234yf feed (100) | Extract (120) | Raffinate (130) | HFC-1234yf product (230) | HF product (190) |
|---|---|---|---|---|---|
| HF, wt % | 14.9 | 0.39 | 8.88 | 0.49 | 100 |
| HFC-1234yf, wt % | 85.1 | 82.5 | 46.7 | 99.5 | 2 ppm |
| Z-HFC-1225ye, wt % | 0 | 17.1 | 44.4 | 130 ppm | 10 ppm |
| Temp, ° C. | −30 | −40 | −40 | −13.5 | 67.2 |
| Pres, psia (kPa) | 164.7 (1136) | 84.7 (584.0) | 84.7 (584.0) | 29.7 (205) | 65.7 (453) |

The above data is calculated for an extractor with 4 theoretical stages operating at a temperature of −40° C. and pressure of 90 psig. The extractant recovery column has 20 theoretical stages, the extract is to the 6$^{th}$ stage from the bottom of the column, and the column operates with a top pressure of 80 psig with 1000 lbs/hour reflux. The raffinate stripping column has 5 theoretical stages, the raffinate is fed to the top stage, and the column operates with a top pressure of 50 psig. The decanter operates at a temperature of 40° C.

The above data is calculated for an extractor with 8 theoretical stages operating at a temperature of −40° C. and pressure of 70 psig. The extractant recovery column has 50 theoretical stages, the extract is fed to the 7$^{th}$ stage from the bottom of the column, and the column operates with a top pressure of 15 psig with 5000 lbs/hour reflux. The raffinate stripping column has 7 theoretical stages, the raffinate is fed to the top stage, and the column operates with a top pressure of 50 psig. The decanter operates at a temperature of −40° C.

Example 6

Example 6 demonstrates that TFE may be separated from HF by liquid-liquid extraction using PMVE (perfluoromethylvinyl ether) as the extractant. A composition comprising 50/50 mole percent HF and TFE is fed to the bottom of an extractor at a rate of 1000 lbs/hour (454 kg/hour). PMVE (extractant) is fed to the top of the extractor at a rate of 500 lbs/hour (227 kg/hour). The data in Table 9 were calculated using measured thermodynamic properties.

TABLE 9

| Component or variable | HF/TFE feed (100) | Extract (120) | Raffinate (130) | TFE product (230) | HF product (190) |
|---|---|---|---|---|---|
| HF, wt % | 16.7 | 0.54 | 71.5 | 0.82 | 100 |
| TFE, wt % | 83.3 | 65.0 | 2.3 | 99.2 | <1 ppm |
| PMVE, wt % | 0 | 34.4 | 26.2 | 10 ppm | <1 ppm |
| Temp, °C. | −20.0 | −30.0 | −30.0 | −32.8 | 67.2 |
| Pres, psia (kPa) | 114.7 (791) | 109.7 (756) | 109.7 (756) | 94.7 (653) | 65.7 (453) |

The above data is calculated for an extractor with 6 theoretical stages operating at a temperature of −30° C. and pressure of 95 psig. The extractant recovery column has 20 theoretical stages, the extract is fed to the 6$^{th}$ stage from the bottom of the column, and the column operates with a top pressure of 80 psig with 1000 lbs/hour reflux. The raffinate stripping column has 5 theoretical stages, the raffinate is fed to the top stage, and the column operates with a top pressure of 50 psig. The decanter operates at a temperature of −30° C.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges include each and every value within that range.

What is claimed is:

1. A process for separating fluoroolefin from a composition comprising HF and fluoroolefin, said process comprising extracting said composition with an extractant, wherein said extractant comprises at least one compound selected from the group consisting of hydrocarbons, chlorocarbons, chlorofluorocarbons, hydrochlorofluorocarbons, hydrofluorocarbons, perfluorocarbons, and perfluorinated ethers, and wherein said fluoroolefin is separated from said mixture by said extractant, and wherein said fluoroolefin comprises compounds with 3 to 10 carbon atoms and is selected from the group consisting of:

(i) fluoroolefins of the formula E- or Z—R1CH=CHR2, wherein R1 and R2 are, independently, C1 to C6 perfluoroalkyl groups;

(ii) cyclic fluoroolefins of the formula cyclo-[CX=CY(CZW)n-], wherein X, Y, Z, and W, independently, are H or F, and n is an integer from 2 to 5; and (iii) fluoroolefins selected from the group consisting of: hexafluoropropene ($CF_3CF=CF_2$); 1,2,3,3,3-pentafluoro-1-propene ($CHF=CFCF_3$), 1,1,3,3,3-pentafluoro-1-propene ($CF_2=CHCF_3$), 1,1,2,3,3-pentafluoro-1-propene ($CF_2=CFCHF_2$), 1,2,3,3-tetrafluoro-1-propene ($CHF=CFCHF_2$), 2,3,3,3-tetrafluoro-1-propene ($CH_2=CFCF_3$), 1,3,3,3-tetrafluoro-1-propene ($CHF=CHCF_3$), 1,1,2,3-tetrafluoro-1-propene ($CF_2=CFCH_2F$), 1,1,3,3-tetrafluoro-1-propene ($CF_2=CHCHF_2$), 1,2,3,3-tetrafluoro-1-propene ($CHF=CFCHF_2$), 3,3,3-trifluoro-1-propene ($CH_2=CHCF_3$), 2,3,3-trifluoro-1-propene ($CHF_2CF=CH_2$); 1,1,2-trifluoro-1-propene ($CH_3CF=CF_2$); 1,2,3-trifluoro-1-propene ($CH_2FCF=CF_2$); 1,1,3-trifluoro-1-propene ($CH_2FCH=CF_2$); 1,3,3-trifluoro-1-propene ($CHF_2CH=CHF$); 1,1,1,2,3,4,4,4-octafluoro-2-butene ($CF_3CF=CFCF_3$); 1,1,2,3,3,4,4,4-octafluoro-1-butene ($CF_3CF_2CF=CF_2$); 1,1,1,2,4,4,4-heptafluoro-2-butene ($CF_3CF=CHCF_3$); 1,2,3,3,4,4,4-heptafluoro-1-butene ($CHF=CFCF_2CF_3$); 1,1,1,2,3,4,4-heptafluoro-2-butene ($CHF_2CF=CFCF_3$); 1,3,3,3-tetrafluoro-2-(trifluoromethyl)-1-propene (($CF_3)_2C=CHF$); 1,1,3,3,4,4,4-heptafluoro-1-butene ($CF_2=CHCF_2CF_3$); 1,1,2,3,4,4,4-heptafluoro-1-butene ($CF_2=CFCHFCF_3$); 1,1,2,3,3,4,4-heptafluoro-1-butene ($CF_2=CFCF_2CHF_2$); 2,3,3,4,4,4-hexafluoro-1-butene ($CF_3CF_2CF=CH_2$); 1,3,3,4,4,4-hexafluoro-1-butene ($CHF=CHCF_2CF_3$); 1,2,3,4,4,4-hexafluoro-1-butene ($CHF=CFCHFCF_3$); 1,2,3,3,4,4-hexafluoro-1-butene ($CHF=CFCF_2CHF_2$); 1,1,2,3,4,4-hexafluoro-2-butene ($CHF_2CF=CFCHF_2$); 1,1,1,2,3,4-hexafluoro-2-butene ($CH_2FCF=CFCF_3$); 1,1,1,2,4,4-hexafluoro-2-butene ($CHF_2CH=CFCF_3$); 1,1,1,3,4,4-hexafluoro-2-butene ($CF_3CH=CFCHF_2$); 1,1,2,3,3,4-hexafluoro-1-butene ($CF_2=CFCF_2CH_2F$); 1,1,2,3,3,4-hexafluoro-1-butene ($CF_2=CFCHFCHF_2$); 3,3,3-trifluoro-2-(trifluoromethyl)-1-propene ($CH_2=C(CF_3)_2$); 1,1,1,2,4-pentafluoro-2-butene ($CH_2FCH=CFCF_3$); 1,1,1,3,4-pentafluoro-2-butene (CF$_3$CH=CFCH$_2$F); 3,3,4,4,4-pentafluoro-1-butene (CF$_3$CF$_2$CH=CH$_2$); 1,1,1,4,4-pentafluoro-2-butene (CHF$_2$CH=CHCF$_3$); 1,1,1,2,3-pentafluoro-2-butene (CH$_3$CF=CFCF$_3$); 2,3,3,4,4-pentafluoro-1-butene (CH$_2$=CFCF$_2$CHF$_2$); 1,1,2,4,4-pentafluoro-2-butene (CHF$_2$CF=CHCHF$_2$); 1,1,2,3,3-pentafluoro-1-butene (CH$_3$CF$_2$CF=CF$_2$); 1,1,2,3,4-pentafluoro-2-butene (CH$_2$FCF=CFCHF$_2$); 1,1,3,3,3-pentafluoro-2-methyl-1-propene (CF$_2$=C(CF$_3$)(CH$_3$)); 2-(difluoromethyl)-3,3,3-trifluoro-1-propene (CH$_2$=C(CHF$_2$)(CF$_3$)); 2,3,4,4,4-pentafluoro-1-butene (CH$_2$=CFCHFCF$_3$); 1,2,4,4,4-pentafluoro-1-butene (CHF=CFCH$_2$CF$_3$); 1,3,4,4,4-pentafluoro-1-butene (CHF=CHCHFCF$_3$); 1,3,3,4,4-pentafluoro-1-butene (CHF=CHCF$_2$CHF$_2$); 1,2,3,4,4-pentafluoro-1-butene (CHF=CFCHFCHF$_2$); 3,3,4,4-tetrafluoro-1-butene (CH$_2$=CHCF$_2$CHF$_2$); 1,1-difluoro-2-(difluoromethyl)-1-propene (CF$_2$=C(CHF$_2$)(CH$_3$)); 1,3,3,3-tetrafluoro-2-methyl-1-propene (CHF=C(CF$_3$)(CH$_3$)); 3,3-difluoro-2-(difluoromethyl)-1-propene (CH$_2$=C(CHF$_2$)$_2$); 1,1,1,2-tetrafluoro-2-butene (CF$_3$CF=CHCH$_3$); 1,1,1,3-tetrafluoro-2-butene (CH$_3$CF=CHCF$_3$); 1,1,1,2,3,4,4,5,5,5-decafluoro-2-pentene (CF$_3$CF=CFCF$_2$CF$_3$); 1,1,2,3,3,4,4,5,5,5-decafluoro-1-pentene (CF$_2$=CFCF$_2$CF$_2$CF$_3$); 1,1,1,4,4,4-hexafluoro-2-(trifluoromethyl)-2-butene ((CF$_3$)$_2$C=CHCF$_3$); 1,1,1,2,4,4,5,5,5-nonafluoro-2-pentene (CF$_3$CF=CHCF$_2$CF$_3$); 1,1,1,3,4,4,5,5,5-nonafluoro-2-pentene (CF$_3$CH=CFCF$_2$CF$_3$); 1,2,3,3,4,4,5,5,5-nonafluoro-1-pentene (CHF=CFCF$_2$CF$_2$CF$_3$); 1,1,3,3,4,4,5,5,5-nonafluoro-1-pentene (CF$_2$=CHCF$_2$CF$_2$CF$_3$); 1,1,2,3,3,4,4,5,5-nonafluoro-1-pentene (CF$_2$=CFCF$_2$CF$_2$CHF$_2$); 1,1,2,3,4,4,5,5,5-nonafluoro-2-pentene (CHF$_2$CF=CFCF$_2$CF$_3$); 1,1,1,2,3,4,4,5,5,5-nonafluoro-2-pentene (CF$_3$CF=CFCHFCF$_2$CHF$_2$); 1,1,1,2,3,4,4,5,5-nonafluoro-2-pentene (CF$_3$CF=CFCHFCF$_3$); 1,2,3,4,4,4-hexafluoro-3-(trifluoromethyl)-1-butene (CHF=CFCF(CF$_3$)$_2$); 1,1,2,4,4,4-hexafluoro-3-(trifluoromethyl)-1-butene (CF$_2$=CFCH(CF$_3$)$_2$); 1,1,1,4,4,4-hexafluoro-2-(trifluoromethyl)-2-butene (CF$_3$CH=C(CF$_3$)$_2$); 1,1,3,4,4,4-hexafluoro-3-(trifluoromethyl)-1-butene (CF$_2$=CHCF(CF$_3$)$_2$); 2,3,3,4,4,5,5-octafluoro-1-pentene (CH$_2$=CFCF$_2$CF$_2$CF$_3$); 1,2,3,3,4,4,5,5-octafluoro-1-pentene (CHF=CFCF$_2$CF$_2$CHF$_2$); 3,3,4,4,4-pentafluoro-2-(trifluoromethyl)-1-butene (CH$_2$=C(CF$_3$)CF$_2$CF$_3$); 1,1,4,4,4-pentafluoro-3-(trifluoromethyl)-1-butene (CF$_2$=CHCH(CF$_3$)$_2$); 1,3,4,4,4-pentafluoro-3-(trifluoromethyl)-1-butene (CHF=CHCF(CF$_3$)$_2$); 1,1,4,4,4-pentafluoro-2-(trifluoromethyl)-1-butene (CF$_2$=C(CF$_3$)CH$_2$CF$_3$); 3,4,4,4-tetrafluoro-3-(trifluoromethyl)-1-butene ((CF$_3$)$_2$CFCH=CH$_2$); 3,3,4,4,5,5,5-heptafluoro-1-pentene (CF$_3$CF$_2$CF$_2$CH=CH$_2$); 2,3,3,4,4,5,5-heptafluoro-1-pentene (CH$_2$=CFCF$_2$CF$_2$CHF$_2$); 1,1,3,3,5,5,5-heptafluoro-1-butene (CF$_2$=CHCF$_2$CH$_2$CF$_3$); 1,1,1,2,4,4,4-heptafluoro-3-methyl-2-butene (CF$_3$CF=C(CF$_3$)(CH$_3$)); 2,4,4,4-tetrafluoro-3-(trifluoromethyl)-1-butene (CH$_2$=CFCH(CF$_3$)$_2$); 1,4,4,4-tetrafluoro-3-(trifluoromethyl)-1-butene (CHF=CHCH(CF$_3$)$_2$); 1,1,1,4-tetrafluoro-2-(trifluoromethyl)-2-butene (CH$_2$FCH=C(CF$_3$)$_2$); 1,1,1,3-tetrafluoro-2-(trifluoromethyl)-2-butene (CH$_3$CF=C(CF$_3$)$_2$); 1,1,1-trifluoro-2-(trifluoromethyl)-2-butene ((CF$_3$)$_2$C=CHCH$_3$); 3,4,4,5,5,5-hexafluoro-2-pentene (CF$_3$CF$_2$CF=CHCH$_3$); 1,1,1,4,4,4-hexafluoro-2-methyl-2-butene (CF$_3$C(CH$_3$)=CHCF$_3$); 3,3,4,5,5,5-hexafluoro-1-pentene (CH$_2$=CHCF$_2$CHFCF$_3$); 4,4,4-trifluoro-2-(trifluoromethyl)-1-butene (CH$_2$=C(CF$_3$)CH$_2$CF$_3$); 1,1,2,3,3,4,4,5,5,6,6,6-dodecafluoro-1-hexene (CF$_3$(CF$_2$)$_3$CF=CF$_2$); 1,1,1,2,2,3,4,5,5,6,6,6-dodecafluoro-3-hexene (CF$_3$CF$_2$CF=CFCF$_2$CF$_3$); 1,1,1,4,4,4-hexafluoro-2,3-bis(trifluoromethyl)-2-butene ((CF$_3$)$_2$C=C(CF$_3$)$_2$); 1,1,1,2,3,4,5,5,5-nonafluoro-4-(trifluoromethyl)-2-pentene ((CF$_3$)$_2$CFCF=CFCF$_3$); 1,1,1,4,4,5,5,5-octafluoro-2-(trifluoromethyl)-2-pentene ((CF$_3$)$_2$C=CHC$_2$F$_5$); 1,1,1,3,4,5,5,5-octafluoro-4-(trifluoromethyl)-2-pentene ((CF$_3$)$_2$CFCF=CHCF$_3$); 3,3,4,4,5,5,6,6,6-nonafluoro-1-hexene (CF$_3$CF$_2$CF$_2$CF$_2$CH=CH$_2$); 4,4,4-trifluoro-3,3-bis(trifluoromethyl)-1-butene (CH$_2$=CHC(CF$_3$)$_3$); 1,1,1,4,4,4-hexafluoro-3-methyl-2-(trifluoromethyl)-2-butene ((CF$_3$)$_2$C=C(CH$_3$)(CF$_3$)); 2,3,3,5,5,5-hexafluoro-4-(trifluoromethyl)-1-pentene (CH$_2$=CFCF$_2$CH(CF$_3$)$_2$); 1,1,1,2,4,4,5,5,5-nonafluoro-3-methyl-2-pentene (CF$_3$CF=C(CH$_3$)CF$_2$CF$_3$); 1,1,1,5,5,5-hexafluoro-4-(trifluoromethyl)-2-pentene (CF$_3$CH=CHCH(CF$_3$)$_2$); 3,4,4,5,5,6,6,6-octafluoro-2-hexene (CF$_3$CF$_2$CF$_2$CF=CHCH$_3$); 3,3,4,4,5,5,6,6-octafluoro1-hexene (CH$_2$=CHCF$_2$CF$_2$CF$_2$CHF$_2$); 1,1,1,4,4-pentafluoro-2-(trifluoromethyl)-2-pentene ((CF$_3$)$_2$C=CHCF$_2$CH$_3$); 4,4,5,5,5-pentafluoro-2-(trifluoromethyl)-1-pentene (CH$_2$=C(CF$_3$)CH$_2$C$_2$F$_5$); 3,3,4,4,5,5,5-heptafluoro-2-methyl-1-pentene (CF$_3$CF$_2$CF$_2$C(CH$_3$)=CH$_2$); 4,4,5,5,6,6,6-heptafluoro-2-hexene (CF$_3$CF$_2$CF$_2$CH=CHCH$_3$); 4,4,5,5,6,6,6-heptafluoro-1-hexene (CH$_2$=CHCH$_2$CF$_2$C$_2$F$_5$); 1,1,1,2,2,3,4-heptafluoro-3-hexene (CF$_3$CF$_2$CF=CFC$_2$H$_5$); 4,5,5,5-tetrafluoro-4-(trifluoromethyl)-1-pentene (CH$_2$=CHCH$_2$CF(CF$_3$)$_2$); 1,1,1,2,5,5,5-heptafluoro-4-methyl-2-pentene (CF$_3$CF=CHCH(CF$_3$)(CH$_3$)); 1,1,1,3-tetrafluoro-2-(trifluoromethyl)-2-pentene ((CF$_3$)$_2$C=CFC$_2$H$_5$); 1,1,1,2,3,4,4,5,5,6,6,7,7,7-tetradecafluoro-2-heptene (CF$_3$CF=CFCF$_2$CF$_2$C$_2$F$_5$); 1,1,1,2,2,3,4,5,5,6,6,7,7-tetradecafluoro-3-heptene (CF$_3$CF$_2$CF=CFCF$_2$C$_2$F$_5$); 1,1,1,3,4,4,5,5,6,6,7,7-tridecafluoro-2-heptene (CF$_3$CH=CFCF$_2$CF$_2$C$_2$F$_5$); 1,1,1,2,4,4,5,5,6,6,7,7-tridecafluoro-2-heptene (CF$_3$CF=CHCF$_2$CF$_2$C$_2$F$_5$); 1,1,1,2,2,4,4,5,5,6,6,7,7-tridecafluoro-3-heptene (CF$_3$CF$_2$CH=CFCF$_2$C$_2$F$_5$); and 1,1,1,2,2,3,5,5,6,6,7,7,7-tridecafluoro-3-heptene (CF$_3$CF$_2$CF=CHCF$_2$C$_2$F$_5$).

2. The process of claim 1, wherein said extracting comprises a liquid-liquid extraction.

3. The process of claim 1 comprising:
   a. feeding a composition comprising HF and fluoroolefin and a composition comprising extractant to an extractor; and
   b. removing from said extractor an extractant-rich phase comprising extractant and fluoroolefin.

4. The process of claim 3 further comprising:
   a. feeding the extractant-rich phase comprising extractant and fluoroolefin to an extractant recovery column; and
   b. recovering fluoroolefin product essentially free of extractant from the extractant recovery column.

5. The process of claim 1 comprising:
a. feeding a composition comprising HF and fluoroolefin and a composition comprising extractant to an extractor; and
b. removing from said extractor an HF-rich phase.

6. The process of claim 5 further comprising:
a. feeding said HF-rich phase to a raffinate stripping column; and
b. recovering from said raffinate stripping column HF product essentially free of fluoroolefin and extractant.

7. The process of claim 1 comprising:
a. feeding a composition comprising HF and fluoroolefin and a composition comprising extractant to an extractor;
b. removing from said extractor an extractant-rich phase comprising extractant and fluoroolefin;
c. removing from said extractor an HF-rich phase;
d. feeding said extractant-rich phase comprising extractant and fluoroolefin to an extractant recovery column;
e. recovering fluoroolefin product essentially free of extractant from the extractant recovery column;
f. feeding said HF-rich phase to a raffinate stripping column; and
g. recovering from said raffinate stripping column HF product essentially free of fluoroolefin and extractant.

8. The process of claim 3, 5, or 7, wherein said extractor operates at a pressure of from about 14.7 psia to about 300 psia and a temperature from about −50° C. to about 150° C.

9. The process of claim 4 or 7, wherein said extractant recovery column operates at a pressure of about 14.7 psia to about 300 psia and a top temperature of about −50° C. to about 100° C. and a bottom temperature of about 50° C. to about 250° C.

10. The process of claim 6 or 7, wherein said raffinate stripping column operates at a pressure of about 14.7 psia to about 100 psia and a top temperature of about −50° C. to about 90° C. and a bottom temperature from about 20° C. to about 100° C.

11. The process of claim 1 wherein said extractant is selected from the group consisting of:
ethane, ethylene, n-propane, propylene, n-butane, isobutane, cyclobutane, 1-butene, 2-butene (cis or trans), n-pentane, isopentane (2-methylbutane), neopentane (2,2-dimethylpropane), cyclopentane, 1-pentene, 2-pentene (cis or trans), cyclopentene, n-hexane, cyclohexane, 2-methylpentane, 3-methylpentane, 1-hexene, 2-hexene (cis or trans), 3-hexene (cis or trans), neohexane (2,2-dimethylbutane), neohexene (3,3-dimethyl-1-butene), 2,2-dimethylbutane, 2,3-dimethylbutane, 2,3-dimethyl-2-butene, 2,3-dimethyl-1-butene, 3,3-dimethyl-1-butene, n-heptane, 1-heptene, 2-heptene (cis or trans), 3-heptene (cis or trans), cycloheptene, octane (all isomers), nonane (all isomers), decane (all isomers), undecane (all isomers), dodecane (all isomers), benzene, toluene, tetrachloroethylene, trichloroethylene, 1,1-dichloroethylene, 1,2-dichloroethylene, carbon tetrachloride (tetrachloromethane), chloroform (trichloromethane), methylene chloride (dichloromethane), 1,1,2,2-tetrachloroethane, 1,1,1,2-tetrachloroethane, 1,1,2-trichloroethane, 1,1,1-trichloroethane, 1,1,1,3,3,3-hexachloropropane, dichlorodifluoromethane (CFC-12), fluorotrichloromethane (CFC-11), fluoropentachloroethane (CFC-111), 1,2-difluoro-1,1,2,2-tetrachloroethane (CFC-112), 1,1-difluoro-1,2,2,2-tetrachloroethane (CFC-112a), 1,1,2-trichloro-1,2,2-trifluoroethane (CFC-113), 1,1,1-trichloro-2,2,2-trifluoroethane (CFC-113a), 1,2-dichloro-1,1,2,2-tetrafluoroethane (CFC-114), 1,1-dichloro-1,2,2,2-tetrafluoroethane (CFC-114a), and chloropentafluoroethane (CFC-115), dichlorofluoromethane (HCFC-21), 1,1,2-trichloro-2,2-difluoroethane (HCFC-122), 2,2-dichloro-1,1,1-trifluoroethane (HCFC-123), 1,2-dichloro-1,1,1-trifluoroethane (HCFC-123a), 2-chloro-1,1,1,2-tetrafluoroethane (HCFC-124), 1-chloro-1,1,2,2-tetrafluoroethane (HCFC-124a), 1-chloro-1,2,2-trifluoroethane (HCFC-133), 2-chloro-1,1,1-trifluoroethane (HCFC-133a), 1,1-dichloro-2-fluoroethane (HCFC-141a), 1,1-dichloro-1-fluoroethane (HCFC-141b), 1-chloro-1,2-difluoroethane (HCFC-142a), 1-chloro-1,1-difluoroethane (HCFC-142b), 1,1,1,2,2,3,4,5,5,6,6,7,7,7-tetradecafluoroheptane (HFC-63-14mcee), 3,3,4,4,5,5,6,6,6-nonafluoro-1-hexene, HFC-162-13mczy, 1,2,3,3,3-pentafluoro-1-propene (HFC-1225ye), 1,1,3,3,3-pentafluoro-1-propene (HFC-1225zc), 1,3,3,3-tetrafluoro-1-propene (HFC-1234ze), 2,3,3,3-tetrafluoro-1-propene (HFC-1234yf), 3,3,3-trifluoro-1-propene(HFC-1243zf), 1,1,1,2,4,4,5,5,5-nonafluoro-2-pentene (HFC-1429myz), 1,1,1,3,4,4,5,5,5-nonafluoro-2-pentene (HFC-1429mzy), 1,1,1,4,4,4-hexafluoro-2-butene (F11E), 1,1,1,4,4,5,5,5-octafluoro-2-pentene (F12E), 1,1,1,2,2,5,5,6,6,7,7,8,8,8-tetradecafluoro-3-octene (F24E), 1,1,1,2,2,3,3,6,6,7,7,8,8,8-tetradecafluoro-4-octene (F33E), fluorobenzene, octafluoropropane (PFC-218), octafluorocyclobutane (PFC-C318), all isomers of $C_4F_{10}$ (PFC-31-10), hexafluoropropylene (HFP, PFC-1216), all isomers of $C_5F_{12}$ (PFC-41-12), all isomers of $C_6F_{14}$ (PFC-51-14), PMVE (perfluoromethylvinylether), PEVE (perfluoroethylvinylether), and mixtures thereof.

12. The process of claim 1, wherein the fluoroolefin comprises a fluoropropene.

13. The process of claim 1, wherein the fluoroolefin is Z-HFC-1225ye, E-HFC-1225ye, or any combination or mixture of both isomers in any ratio.

14. The process of claim 1, wherein the fluoroolefin is HFC-1234yf.

15. The process of claim 1, wherein the fluoroolefin is Z-HFC-1234ze, E-HFC-1234ze, or any combination or mixture of both isomers in any ratio.

16. The process of claim 1, wherein said fluoroolefin is selected from the group consisting of:
1,1,1,4,4,4-hexafluorobut-2-ene; 1,1,1,4,4,5,5,5-octafluoropent-2-ene; 1,1,1,4,4,5,5,6,6,6-decafluorohex-2-ene; 1,1,1,4,5,5,5-heptafluoro-4-(trifluoromethyl)pent-2-ene; 1,1,1,2,2,5,5,6,6,6-decafluorohex-3-ene; 1,1,1,4,4,5,5,6,6,7,7,7-dodecafluorohept-2-ene; 1,1,1,4,4,5,6,6,6-nonafluoro-5-(trifluoromethyl)hex-2-ene; 1,1,1,4,5,5,6,6,6-nonfluoro-4-(trifluoromethyl)hex-2-ene; 1,1,1,5,5,5-hexafluoro-4,4-bis(trifluoromethyl)pent-2-ene; 1,1,1,2,2,5,5,6,6,7,7,7-dodecafluorohept-3-ene; 1,1,1,2,2,5,6,6,6-nonafluoro-5-(trifluoromethyl)hex-3-ene; 1,1,1,4,4,5,5,6,6,7,7,8,8,8-tetradecafluorooct-2-ene; 1,1,1,4,4,5,5,6,7,7,7-undecafluoro-6-(trifluoromethyphept-2-ene; 1,1,1,5,5,6,6,6-octafluoro-4,4-bis(trifluoromethyl)hex-2-ene; 1,1,1,2,2,5,5,6,6,7,7,8,8,8-tetradecafluorooct-3-ene; 1,1,1,2,2,5,5,6,7,7,7-undecafluoro-6-(trifluoromethyl)hept-3-ene; 1,1,1,2,2,5,6,6,7,7,7-undecafluoro-5-(trifluoromethyl)hept-3-ene; 1,1,1,2,2,6,6,6-octafluoro-5,5-bis(trifluoromethyl)hex-3-ene; 1,1,1,2,2,3,3,6,6,7,7,8,8,8-tetradecafluorooct-4-ene; 1,1,1,2,5,6,6,6-octafluoro-2,5-bis(trifluoromethyl)hex-3-ene; 1,1,1,2,5,5,6,6,7,7,7-undecafluoro-2-(trifluoromethyl)hept-3-ene; 1,1,1,4,4,5,5,6,6,7,7,8,8,9,9,9-hexadecafluoronon-2-ene; 1,1,1,4, 5,5,6,6,7,7,8,8,8-tridecafluoro-4-(trifluoromethyl)hept-2-ene; 1,1,1,6,6,6-octafluoro-4,4-bis(trifluoromethyl)hept-2-ene; 1,1,1,2,2,5,5,6,6,7,7,8,8,9,9,9-hexadecafluoronon-3-ene; 1,1,1,2,2,5,5,6,6,7,8,8,8-tridecafluoro-7-(trifluoromethyl)oct-3-ene; 1,1,1,2,2,6,6,7,7,7-decafluoro-5,5-bis(trifluoromethyl)hept-3-ene; 1,1,1,2,2,3,3,6,6,7,7,8,8,9,9,9-hexadecafluoronon-4-ene; 1,1,1,2,2,3,3,6,6,7,8,8,8-tridecafluoro-7-(trifluoromethyl)oct-4-ene; 1,1,1,2,2,3,3,6,7,7,8,8,8-tridecafluoro-6-(trifluoromethyl)oct-4-ene; 1,1,1,5,5,6,6,7,7,7-decafluoro-2,2-bis(trifluoromethyl)hept-3-ene; 1,1,1,2,5,5,6,6,7,7,8,8,8-tridecafluoro-2(trifluoromethyl)oct-3-ene; 1,1,1,2,5,5,6,7,7,7-decafluoro-2,6-bis(trifluoromethyl)hept-3-ene; 1,1,1,2,5,6,6,7,7,7-decafluoro-2,5-bis(trifluoromethyl)hept-3-ene; 1,1,1,2,6,6,6-heptafluoro-2,5,5-tris(trifluoromethyl)hex-3-ene; 1,1,1,2,2,5,5,6,6,7,7,8,8,9,9,10,10,10-octadecafluorodec-3-ene; 1,1,1,2,2,5,6,6,7,7,8,8,9,9,9-pentadecafluoro-5-(trifluoromethyl)non-3-ene; 1,1,1,2,2,6,6,7,7,8,8-dodecafluoro-5,5-bis(trifluoromethyl)oct-3-ene; 1,1,1,2,2,3,3,6,6,7,7,8,8,9,9,10,10,10-octadecafluorodec-4-ene; 1,1,1,2,2,3,3,6,6,7,7,8,9,9,9-pentadecafluoro-8-(trifluoromethyl)non-4-ene; 1,1,1,2,2,3,3,7,7,8,8,8-dodecafluoro-6,6-bis(trifluoromethyl)oct-4-ene; 1,1,1,2,5,5,6,6,7,7,8,8,9,9,9-pentadecafluoro-2-(trifluoromethyl)non-3-ene; 1,1,1,2,5,5,6,6,7,8,8,8-dodecafluoro-2,7-bis(trifluoromethyl)oct-3-ene; 1,1,1,2,6,6,7,7,7-nonafluoro-2,5,5-tris(trifluoromethyl)hept-3-ene; 1,1,1,2,2,3,3,4,4,7,7,8,8,9,9,10,10,10-octadecafluorodec-5-ene; 1,1,1,2,3,3,6,6,7,7,8,8,9,9,9-pentadecafluoro-2-(trifluoromethyl)non-4-ene; 1,1,1,2,2,3,6,6,7,7,8,8,9,9,9-pentadecafluoro-3-(trifluoromethyl)non-4-ene; 1,1,1,5,5,6,6,7,7,8,8,8-dodecafluoro-2,2,-bis(trifluoromethyl)oct-3-ene; 1,1,1,2,3,3,6,6,7,8,8,8-dodecafluoro-2,7-bis(trifluoromethyl)oct-4-ene; 1,1,1,2,3,3,6,7,7,8,8,8-dodecafluoro-2,6-bis(trifluoromethyl)oct-4-ene; 1,1,1,5,5,6,7,7,7-nonafluoro-2,2,6-tris(trifluoromethyl)hept-3-ene; 1,1,1,2,2,3,6,7,7,8,8,8-dodecafluoro-3,6-bis(trifluoromethyl)oct-4-ene; 1,1,1,2,2,3,6,7,7,8,8,8-dodecafluoro-3,6-bis(trifluoromethyl)oct-4-ene; 1,1,1,5,6,6,7,7,7-nonafluoro-2,2,5-tris(trifluoromethyl)hept-3-ene; and 1,1,1,6,6,6-hexafluoro-2,2,5,5-tetrakis(trifluoromethyl)hex-3-ene.

17. The process of claim 1, wherein said fluoroolefin is selected from the group consisting of:
1,2,3,3,4,4-hexafluorocyclobutene; 3,3,4,4-tetrafluorocyclobutene; 3,3,4,4,5,5,-hexafluorocyclopentene; 1,2,3,3,4,4,5,5-octafluorocyclopentene; and 1,2,3,3,4,4,5,5,6,6-decafluorocyclohexene.

* * * * *